(12) United States Patent
Khashayar

(10) Patent No.: US 7,640,119 B2
(45) Date of Patent: *Dec. 29, 2009

(54) SYSTEM FOR DYNAMICALLY ADJUSTING OPERATION OF A SURGICAL HANDPIECE

(75) Inventor: Amir H. Khashayar, Chino Hills, CA (US)

(73) Assignee: Alcon, Inc., Hunenberg (CH)

(*) Notice: Subject to any disclaimer, the term of this patent is extended or adjusted under 35 U.S.C. 154(b) by 472 days.

This patent is subject to a terminal disclaimer.

(21) Appl. No.: 11/479,224

(22) Filed: Jun. 30, 2006

(65) Prior Publication Data

US 2008/0122407 A1    May 29, 2008

(51) Int. Cl.
G01R 15/00 (2006.01)
G01R 19/00 (2006.01)
(52) U.S. Cl. ............................ 702/57; 702/64
(58) Field of Classification Search .......... 702/57, 702/60, 64, 85, 58, 61, 65, 107; 606/38, 606/42
See application file for complete search history.

(56) References Cited

U.S. PATENT DOCUMENTS

| | | | |
|---|---|---|---|
| 1,493,450 | A | 5/1924 | Richardson |
| 3,589,363 | A | 6/1971 | Banko et al. |
| 3,606,878 | A | 9/1971 | Kellog, Jr. |
| 3,818,913 | A | 6/1974 | Wallach |
| 3,930,505 | A | 1/1976 | Wallach |
| 3,994,297 | A | 11/1976 | Kopf |
| 4,024,866 | A | 5/1977 | Wallach |
| 4,223,676 | A | 9/1980 | Wuchinich et al. |
| 4,246,902 | A | 1/1981 | Martinez |
| 4,249,899 | A | 2/1981 | Davis |
| 4,265,618 | A | 5/1981 | Herskovitz et al. |
| 4,301,802 | A | 11/1981 | Poler |
| 4,493,694 | A | 1/1985 | Wuchinich |
| 4,515,583 | A | 5/1985 | Sorich |
| 4,517,977 | A | 5/1985 | Frost |
| 4,570,632 | A | 2/1986 | Woods |
| 4,577,629 | A | 3/1986 | Martinez |
| 4,589,414 | A | 5/1986 | Yoshida et al. |
| 4,589,415 | A | 5/1986 | Haaga |

(Continued)

FOREIGN PATENT DOCUMENTS

EP    1157667 A2    11/2001

(Continued)

OTHER PUBLICATIONS

European Application No. 07110500.1, Publication No. 1905359, 34 pages.

(Continued)

Primary Examiner—Michael P Nghiem
(74) Attorney, Agent, or Firm—Russell Henrichs

(57) ABSTRACT

In some embodiments, a method of adjusting the amount of energy delivered to a liquefaction handpiece of an ophthalmic surgical system may include monitoring a voltage source at an output of a charging element of the ophthalmic surgical system, dynamically adjusting the charging element output based on feedback from the monitored voltage source, and dynamically adjusting the amount of energy provided by the voltage source as an input to the liquefaction handpiece. The energy adjustment may be based on the adjusted charging element output.

42 Claims, 21 Drawing Sheets

U.S. PATENT DOCUMENTS

| | | |
|---|---|---|
| 4,609,368 A | 9/1986 | Dotson, Jr. |
| 4,662,869 A | 5/1987 | Wright |
| 4,674,502 A | 6/1987 | Imonti |
| 4,696,298 A | 9/1987 | Higgins et al. |
| 4,706,669 A | 11/1987 | Schlegel |
| 4,753,234 A | 6/1988 | Martinez |
| 4,862,889 A | 9/1989 | Feucht |
| 4,869,715 A | 9/1989 | Sherburne |
| 4,909,249 A | 3/1990 | Akkas et al. |
| 4,911,161 A | 3/1990 | Schechter |
| 4,922,902 A | 5/1990 | Wuchinich et al. |
| 4,986,827 A | 1/1991 | Akkas et al. |
| 4,989,583 A | 2/1991 | Hood |
| 5,019,035 A | 5/1991 | Missirlian et al. |
| 5,106,364 A | 4/1992 | Hayafuji et al. |
| 5,154,694 A | 10/1992 | Kelman |
| 5,226,910 A | 7/1993 | Kajiyama et al. |
| 5,250,065 A | 10/1993 | Clement et al. |
| 5,261,883 A | 11/1993 | Hood et al. |
| 5,261,923 A | 11/1993 | Soares |
| 5,275,607 A | 1/1994 | Lo et al. |
| 5,284,472 A | 2/1994 | Sussman et al. |
| 5,285,795 A | 2/1994 | Ryan et al. |
| 5,322,504 A | 6/1994 | Doherty et al. |
| 5,331,951 A | 7/1994 | Kepley |
| 5,359,996 A | 11/1994 | Hood |
| 5,422,567 A | 6/1995 | Matsunaga |
| 5,423,330 A | 6/1995 | Lee |
| 5,562,692 A | 10/1996 | Bair |
| 5,591,184 A | 1/1997 | McDonnell et al. |
| 5,616,120 A | 4/1997 | Andrew et al. |
| 5,624,392 A | 4/1997 | Saab |
| 5,624,393 A | 4/1997 | Diamond |
| 5,653,692 A | 8/1997 | Masterson et al. |
| 5,669,923 A | 9/1997 | Gordon |
| 5,674,226 A | 10/1997 | Doherty et al. |
| 5,735,815 A | 4/1998 | Bair |
| 5,766,194 A | 6/1998 | Smith |
| 5,865,790 A | 2/1999 | Bair |
| 5,879,247 A | 3/1999 | Winter et al. |
| 5,891,095 A | 4/1999 | Eggers et al. |
| 5,938,677 A * | 8/1999 | Boukhny et al. ............ 606/169 |
| 5,947,988 A | 9/1999 | Smith |
| 6,093,186 A | 7/2000 | Goble |
| 6,139,571 A | 10/2000 | Fuller et al. |
| 6,203,516 B1 | 3/2001 | Kepley |
| 6,394,974 B1 | 5/2002 | Kadziauskas et al. |
| 6,440,103 B1 | 8/2002 | Hood et al. |
| 6,648,847 B2 | 11/2003 | Sussman et al. |
| 7,044,571 B2 * | 5/2006 | Smith et al. .................. 347/10 |
| 2005/0261628 A1 * | 11/2005 | Boukhny et al. ............ 604/118 |
| 2007/0215585 A1 * | 9/2007 | O'Connor ................ 219/130.1 |
| 2008/0097428 A1 * | 4/2008 | Khashayar .................. 606/42 |

FOREIGN PATENT DOCUMENTS

| | | |
|---|---|---|
| EP | 1157667 A3 | 7/2003 |
| WO | WO 96/24314 | 8/1996 |

OTHER PUBLICATIONS

Office Action dated May 29, 2009 for U.S. Appl. No. 11/479,666, Khashayar, Entitled: System for Dynamically Adjusting Operation of a Surgical Handpiece, filed Jun. 30, 2006, 13 pages.

\* cited by examiner

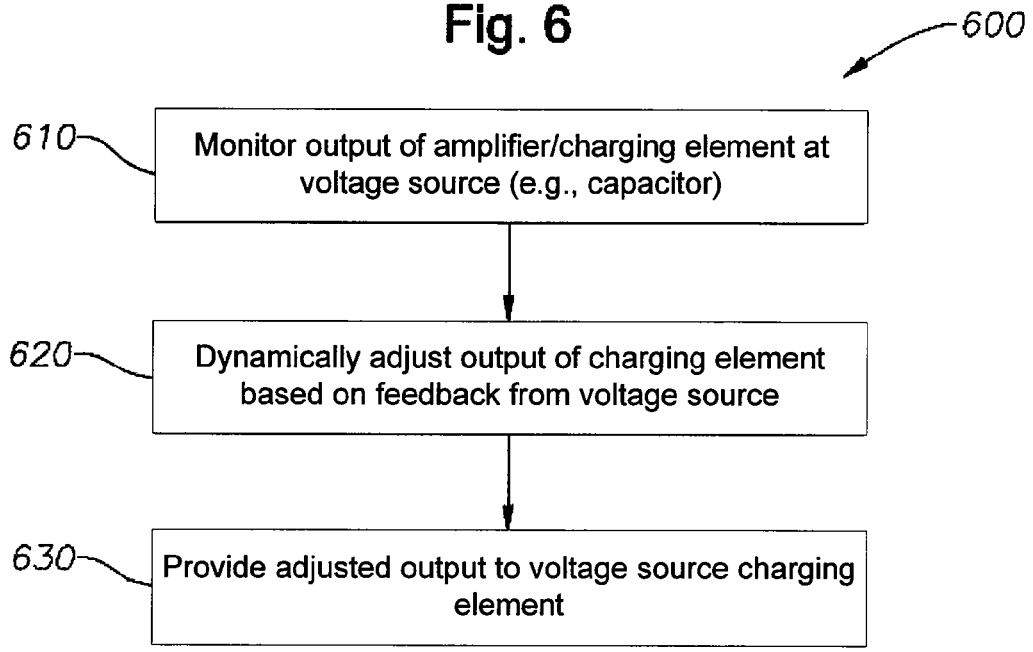
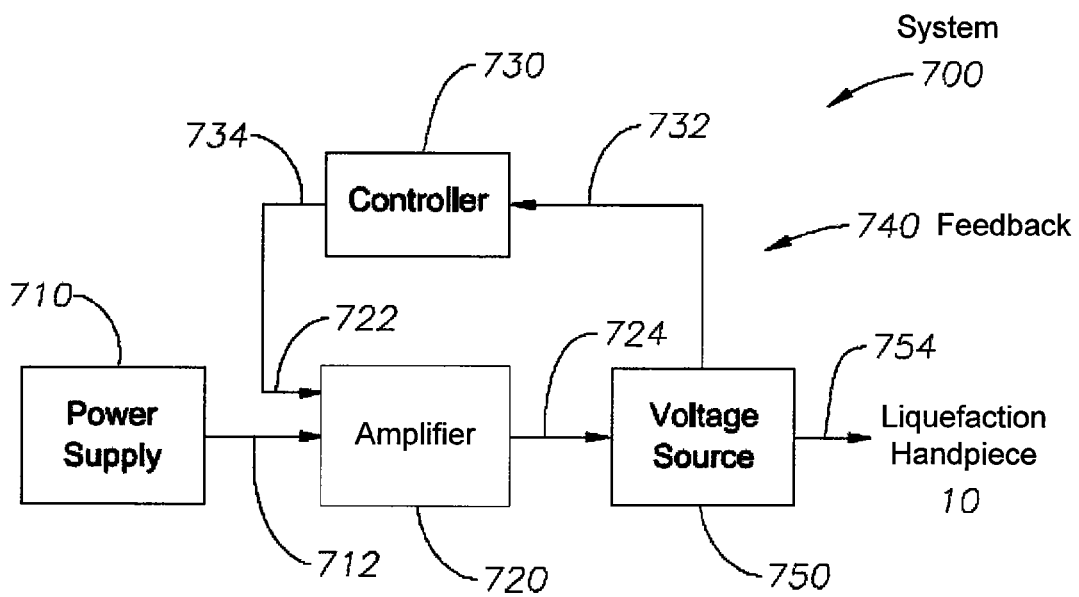

| 1022 | 1032 |
|---|---|
| $\Delta V$ | $\frac{dv}{dt}$ |
| $\Delta V_1$ | $\frac{dv}{dt}\ 1$ |
| $\Delta V_2$ | $\frac{dv}{dt}\ 2$ |
| $\Delta V_3$ | $\frac{dv}{dt}\ 3$ |
| $\Delta V_N$ | $\frac{dv}{dt}\ N$ |

1030 Table

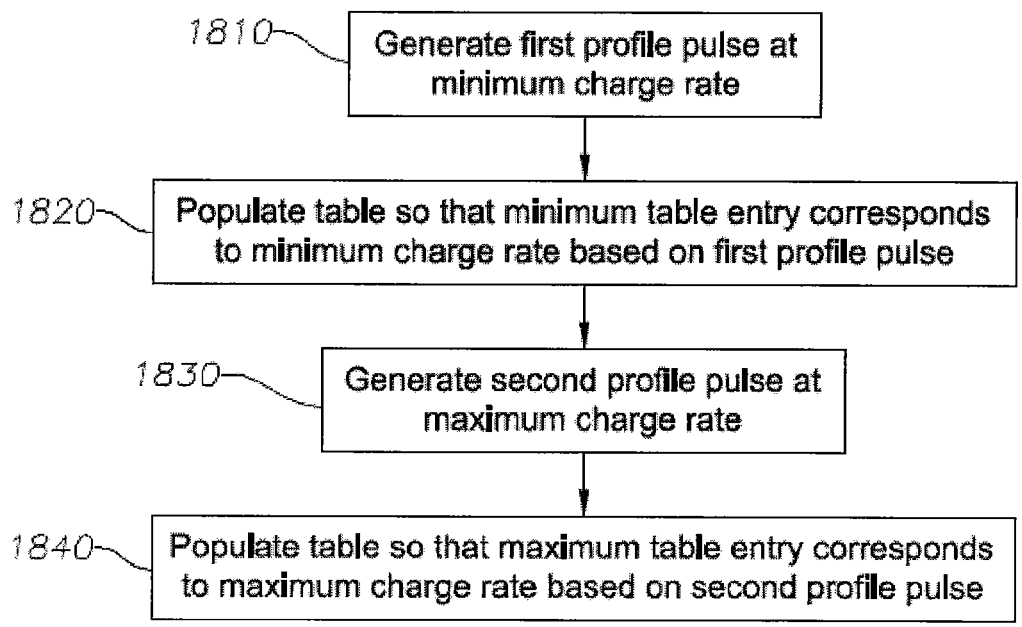
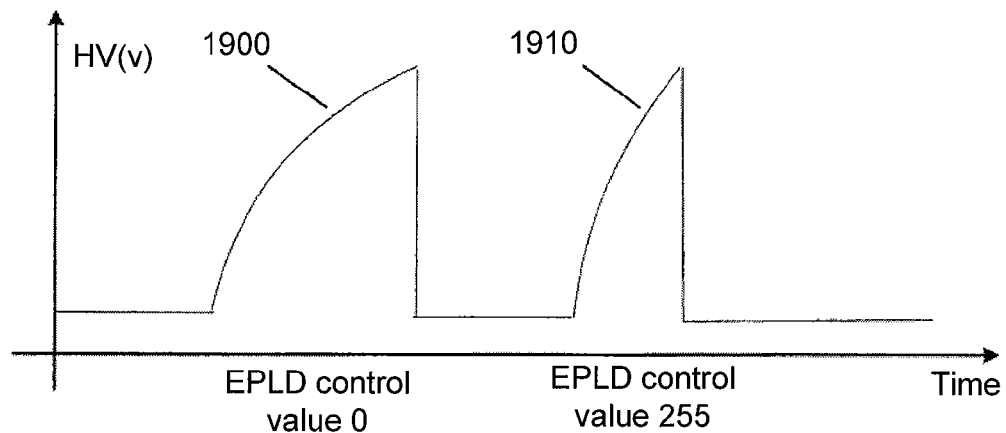

Undershoot
$\Delta_V$ (Desired) = 10 Volts
$V_{RECHARGE}$ = 8 Volts
$\Delta V_{RECHARGE}$ = 2 Volts

| 1022 | 1032 |
|---|---|
| $\Delta V$ | $\frac{dv}{dt}$ |
| $\Delta V_A$ | $\frac{dv}{dt} - x$ |
| $\Delta V_B$ | $\frac{dv}{dt} + y$ |
| ⋮ | ⋮ |

SYSTEM FOR DYNAMICALLY ADJUSTING OPERATION OF A SURGICAL HANDPIECE

FIELD OF THE INVENTION

The present invention relates generally to the field of ophthalmic surgery and, more particularly, to a system and method for dynamically adjusting energy delivered to a surgical handpiece.

BACKGROUND

The human eye functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates because of the is diminished light that can be transmitted to the retina. This deficiency is medically known as a cataract. An accepted treatment for cataracts is to surgically remove the cataract and replace the diseased lens with an artificial intraocular lens (IOL). In the United States, most cataractous lenses are removed using a surgical technique called phacoemulsification. During this procedure, a thin cutting tip or needle is inserted into the diseased lens and vibrated ultrasonically. The vibrating cutting tip liquefies or emulsifies the lens, which is aspirated out of the eye. The diseased lens, once removed, is replaced by an IOL.

More recently, water-jet based liquefaction devices that generate pulses of heated surgical solution have been introduced for cataract surgery and other ophthalmic procedures and treatments. Liquefaction handpieces heat a balanced salt solution, and the heated solution removes the cataractous lens. For example, FIG. 1 generally illustrates an AquaLase® handpiece, available from Alcon Laboratories, Forth Worth, Tex. The device or handpiece assembly 10 (generally "handpiece") shown in FIG. 1 includes a body 11, such as a titanium handpiece body, a tip 12, such as a polymer tip, an irrigation sleeve 13, an aspiration line 14, a solution line 15, e.g., for a balanced salt solution, and an irrigation line 16.

The tip 12 is disposed at the end of the handpiece 10. The irrigation sleeve 12, is placed over the tip 12 to provide an environment for irrigation solution to be delivered to the eye via the irrigation line 16. The aspiration line 14 carries fluid that is drawn from the eye by a vacuum, and the solution line 15 delivers a heated balanced salt solution, which breaks apart the cataract. Irrigation fluid is delivered through the irrigation line 16 and flushes cataractous material that is removed or broken by the balanced salt solution.

Referring to FIGS. 2A and 2B, in use, the distal end of the tip 12 is placed within a cataract 20 in an eye 21 and propels pulses of heated solution 22 through the tip 12 and at the cataract 20. Each pulse 22 can include about four microliters of solution 22. The solution 22 is heated by heating elements 23 within the handpiece 10 as the solution 22 passes between the elements 23 and through the handpiece body 11. The amount of energy 24 provided to the handpiece 10 is a factor that controls the temperature of the heating elements 23 and the heating of the solution 22. The pulses of warmed solution 22 impact the cataract 20, resulting in liquefaction, during which the cataract 20 is eroded or dissolved. Cataract material 20 can then be washed and aspirated from the eye 21.

Liquefaction handpieces provide a number of advantages over other surgical systems and handpieces. For example, since liquefaction handpieces do not involve ultrasonic motion, they facilitate a watertight incision in the eye and provide various safety advantages, including reduced risk of capsule rupture and reduced eye turbulence. Liquefaction handpieces also typically operate at lower temperatures compared to other handpieces (since they do not have any moving parts), thus reducing thermal stress to the eye. Liquefaction handpieces can also be easier for a surgeon to control and manipulate. While liquefaction has been successfully used and provides various benefits and alternative surgical solutions, the manner in which energy is delivered to the handpiece can be improved to provide improved control over the solution pulses delivered to the cataract.

Referring to FIGS. 3 and 4, one known liquefaction handpiece includes a mechanism that is responsible for controlling the operation and the handpiece and control parameters. The mechanism includes an amplifier or engine 30 that produces "High-Voltage" (HV) energy 31. FIG. 4 illustrates HV energy as a continuous series of pulses 31. A gating mechanism or other suitable component 32 generates a series of control or RF Enable pulses (RFEN) 33. The control pulses 33 define an active period 34 and an inactive period 35. The active period 34 serves as a gate to pass pulses 31 from the HV engine 30, whereas pulses 31 are not provided as an output during the inactive period 35, resulting in a series of HV pulses 33 that are provided to the liquefaction handpiece device 10.

It is important to control, maintain, and monitor the amount of HV energy that is generate by the engine 30 and applied and utilized by the handpiece 10 for optimum handpiece 10 operation. Theoretical handpiece operation is based on a constant voltage source, the output of which is provided to a capacitor that is charged and periodically discharged to provide energy to the handpiece in a series of controlled pulses. Referring to FIG. 5, HV energy, therefore, is required to be present only for those instances where the energy is applied to the handpiece using the RFEN pulses 33 during a burst signal or window 50. The combination of software and hardware support provides a virtual constant voltage for the handpiece.

With the controls shown in FIGS. 3-5, capacitors must be fully charged by the time a control pulse triggers discharge of a capacitor to provide stored energy to the handpiece. Known systems typically charge capacitors as quickly as possible to ensure that the capacitors are sufficiently charged or provide a constant voltage source through a transformer, which can be large and bulky, e.g., about 12"×12". Further, capacitors are charged as quickly as possible since the circuit can be easily implemented by pre-setting the charge rate. As a result, however, at the beginning of a capacitor recharge cycle, charging the capacitor as quickly as possible results in a current spike, which can complicate circuit design and reduce circuit performance and place unnecessary burdens on the system power source.

While known control and recharging systems has been used effectively in the past to drive liquefaction handpieces, they can be improved by using feedback to adjust and adapt operating parameters that are suitable for different handpieces and handpiece components. Systems should also be able to adapt to different components and their operation rather than relying on preset operating parameters that cannot be adjusted. Further, known systems can be improved by allowing for system adjustments that more accurately reflect actual operation of system components. Systems should also be more efficient by reducing or eliminating current spikes in favor of more gradual current transitions. Embodiments of the invention fulfill these unmet needs.

SUMMARY

In accordance with one embodiment of the invention, a method of adjusting the amount of energy delivered to a liquefaction handpiece of an ophthalmic surgical system includes monitoring a voltage source at an output of a charging element of the ophthalmic surgical system, dynamically adjusting the charging element output based on feedback from the monitored voltage source, and dynamically adjusting the amount of energy provided by the voltage source as an input to the liquefaction handpiece. The energy adjustment is based on the adjusted charging element output.

In accordance with another embodiment, a method of controlling the amount of energy delivered to a liquefaction handpiece of an ophthalmic surgical system based on feedback includes monitoring a voltage of a voltage source at an output of a charging element of the ophthalmic surgical system to determine a first voltage of the voltage source at a first time and a second voltage of the voltage source at a second time. The first voltage is converted from a first analog value to a first digital value. The second voltage is converted from a second analog value to a second digital value. The difference between the first and second digital voltage values is determined, and a table is used to determine a rate at which a voltage of the charging element output changes over time based on the determined difference between digital voltage values. The table identifies rates at which a voltage of the charging element output increases over time corresponding to determined differences between digital values. The output of the charging element is, in turn, adjusted based on the determined rate from the table, and the amount of energy provided by the voltage source as an input of the liquefaction handpiece is adjusted based on the adjusted charging element output.

In accordance with another alternative embodiment, a method of adjusting the amount of energy delivered to a liquefaction handpiece of an ophthalmic surgical system based on feedback includes generating a table that relates differences between digital voltage values to dv/dt. A dv/dt value is a rate of change of a voltage of the output of a charging element of the ophthalmic surgical system over time. A minimum value of the table is based on a first profile pulse and the time that is required for the first profile pulse to reach a predetermined voltage, and a maximum value of the table is based on a second profile pulse and the time that is required for the second profile pulse to reach the predetermined voltage. The voltage of voltage source at the output of the charging element output is monitored to determine a first voltage value of the voltage source at a first time and a second voltage value of the voltage source at a second time. The first voltage value is converted to a first digital value, and the second voltage value is converted to a second digital value. The difference between the first and second digital voltage values is determined. Using the table, a dv/dt value corresponding to the determined difference is determined, and the dv/dt of the charging element output is dynamically adjusted based on the determined dv/dt value from the table. The amount of energy provided by the voltage source as an input to the liquefaction handpiece is dynamically adjusted based on the adjusted charging element output.

In yet a further embodiment, a system for controlling the amount of energy delivered to a liquefaction handpiece of an ophthalmic surgical system includes a power supply, a charging element, a voltage source and a controller. The power supply drives the charging element, and the voltage source is at the output of the charging element. The voltage source monitored, and the resulting data is provided to the controller, which generates an output that is provided to the charging element to dynamically adjust the charging element output which, in turn, dynamically adjusts the amount of energy provided by the voltage source as an input to the liquefaction handpiece.

According to another alternative embodiment of the invention, a system for controlling the amount of energy delivered to a liquefaction handpiece of an ophthalmic surgical system includes a power supply, a charging element and a voltage source. The power supply drives the charging element, and the voltage source is monitored to determine a first voltage value at a first time and a second voltage value at a second time. The controller converts the first voltage to a first digital value and the second voltage to a second digital value. The controller also determines a difference between the first and second digital voltage values, and performs a look-up in a table that correlates determined differences and outputs of the charging element. Based on data obtained from the table, the charging element output is dynamically adjusted, and the amount of energy provided by the voltage source as an input to the liquefaction handpiece is dynamically adjusted based on the adjusted charging element output.

In yet another alternative embodiment, a system for controlling the amount of energy delivered to a liquefaction handpiece of an ophthalmic surgical system includes a power supply, a charging element, a voltage source and a controller. The power supply drives the charging element, the voltage source is monitored. The monitored data is provided to the controller. The system also includes a table that correlates values representing the difference between monitored voltages and dv/dt, which is a rate of change of the voltage of the output of the charging element over time. The table is populated with values including a minimum value, which is based on a first profile pulse and the time that is required for the first profile pulse to reach a predetermined voltage. The table is also populated with a maximum value, which is based on a second profile pulse and the time that is required for the second profile pulse to reach the predetermined voltage. The controller receives as inputs from the voltage source a first voltage at a first time and a second voltage at a second time and converts these values into first and second digital values. The controller determines a difference between the first and second digital voltage values, and using the determined difference, performs a look-up in the table to determine a dv/dt value. The result of the table look-up is used to dynamically adjust the charging element which, in turn, dynamically adjusts the amount of energy provided by the voltage source as an input to the liquefaction handpiece.

In various embodiments, the voltage source that is monitored is a capacitor. The amount of energy provided by the capacitor to the liquefaction handpiece is dynamically adjusted. Adjustments include adjusting for undershoot or overshoot. Undershoot occurs when the capacitor is charged to a level that is less than a predetermined level after a predetermined time, and overshoot occurs when the capacitor is charged to a level that is greater than a predetermined level after a predetermined time. Energy stored by a capacitor is provided to the liquefaction handpiece during one or more control pulses, and recharged by the charging element between control pulses. In this manner, the capacitor is charged and recharged to provide sufficient energy to the liquefaction handpiece, which may involve fully recharging the capacitor. Embodiments advantageously achieve these improvements automatically without user input.

In various embodiments, the difference calculation between digital values involves initially reducing the first voltage and reducing the second voltage to lower levels, e.g., to a value between 0-5 volts. The first and second reduced analog values are then converted to digital values, and the difference between the resulting first and second digital values is determined and used as feedback to the charging element.

Also in various embodiments, a table is used to store determined differences between digital values and corresponding rates at which a voltage of the charging element output increases. This information is used to control and adjust the charging element which, in turn, adjusts the output of the charging element, the charging of the voltage source, and the energy provided by the voltage source. The table can be pre-programmed or automatically generated at power up of the ophthalmic surgical system. According to one embodiment, the table is generated by generating a first profile pulse that is based on a minimum value of the table and a time that is required for the pulse to reach a predetermined voltage and generating a second profile pulse that is based on a maximum value of the table and a time that is required for the pulse to reach the predetermined voltage. The second profile pulse reaching the predetermined voltage faster than the first profile pulse. Values between table entries can be determined by interpolation or other suitable methods. Table values can also be updated to reflect actual operation of the system.

Also in various embodiments, a table correlating difference values to dv/dt values can be stored in a programmable logic device of a controller.

BRIEF DESCRIPTION OF THE DRAWINGS

Referring now to the drawings, in which like reference numbers represent corresponding parts throughout, and in which:

FIG. 6 is a flow chart illustrating a method for adjusting the amount of energy delivered to a liquefaction handpiece according to one embodiment;

FIG. 7 is a block diagram of a system for adjusting the amount of energy delivered to a liquefaction handpiece using feedback according to one embodiment;

FIG. 18 is a flow chart illustrating a method of populating a table using profile pulses according to one embodiment;

FIG. 19 illustrates two profile pulses according to one embodiment;

DETAILED DESCRIPTION OF ILLUSTRATED EMBODIMENTS

Figure 1:
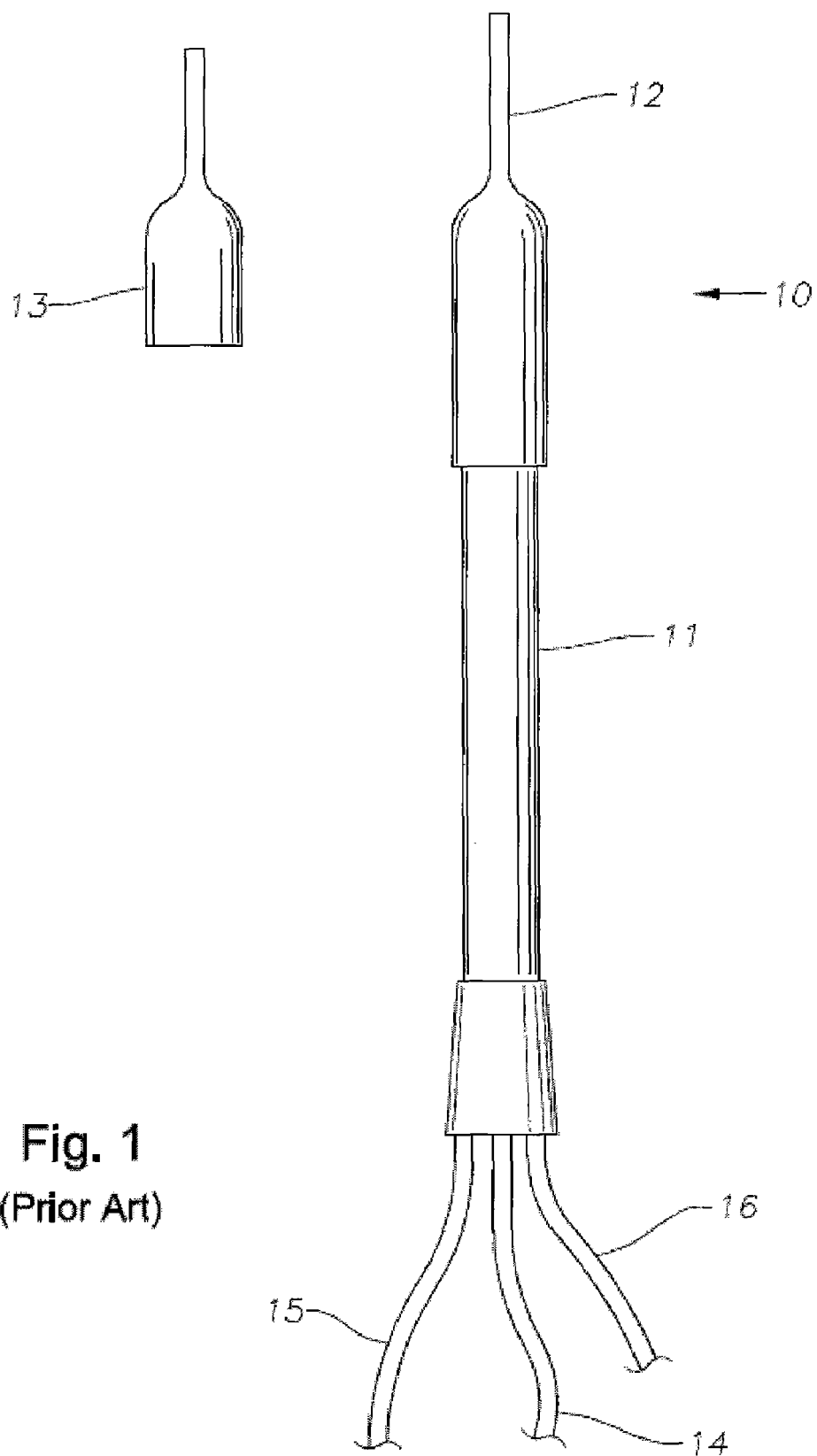
FIG. 1 illustrates an exemplary liquefaction handpiece that can be controlled using embodiments of the invention.
Figure 2A:
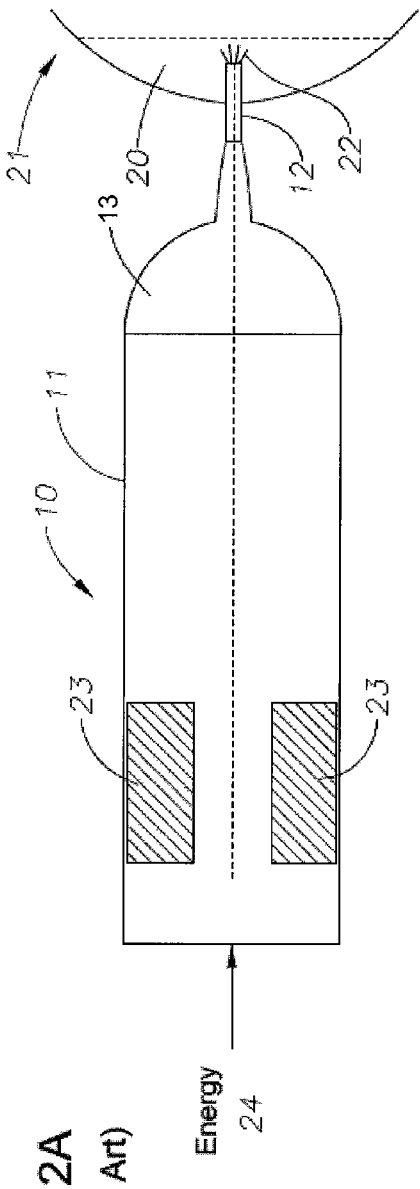
FIG. 2A illustrates use of an exemplary liquefaction handpiece to remove a cataract.
Figure 2B:
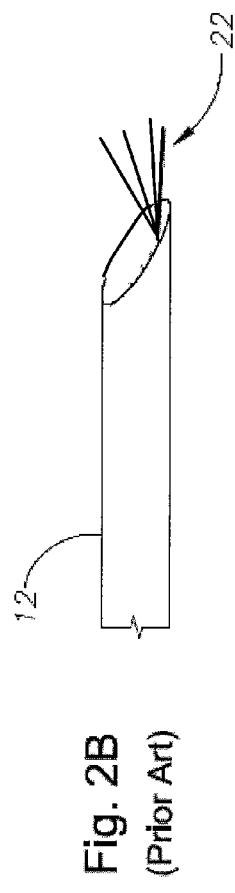
FIG. 2B illustrates delivery of solution through a tip of an exemplary liquefaction handpiece in further detail.
Figure 3:
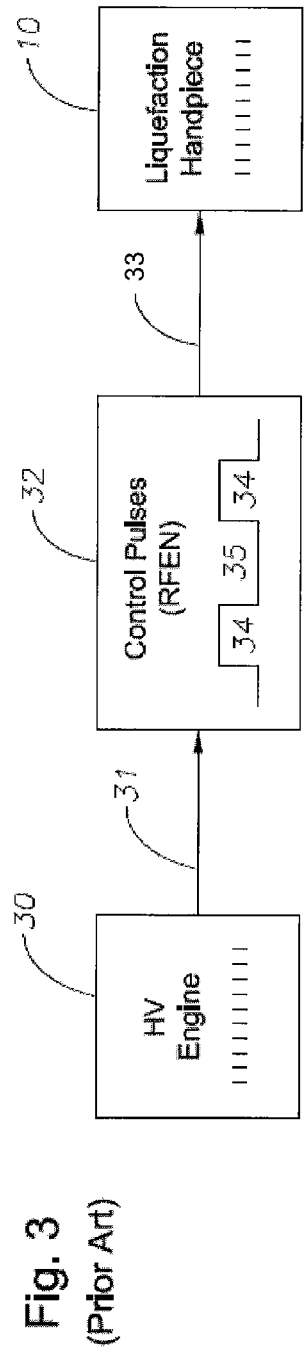
FIG. 3 is a block diagram generally illustrating a known system for driving a liquefaction handpiece.

Embodiments of the invention provide methods and systems for dynamically adjusting the amount of energy delivered to a liquefaction handpiece using feedback. The output of a charging element, such as a trickle charger and regulator or amplifier (generally "charging element"), is monitored. For example, the voltage source, such as a capacitor at the output of charging element, is monitored. Monitored data is processed if necessary and provided to a controller, which uses the feedback data to dynamically adjust the output of the charging element, adjust the rate at which voltage of the output of the charging element increases over time. The adjusted output recharges the capacitor which, in turn, dynamically adjusts the amount of energy delivered to the liquefaction handpiece. Embodiments advantageously use feedback to track and compare outputs of the charging element and make adjustments as needed to provide more accurate control over the energy provided to liquefaction handpieces. Embodiments also provide for more energy efficient handpiece operation. Further, embodiments advantageously eliminate the need to charge voltage sources, such as capacitors, as quickly as possible or at a set rate that cannot be adjusted since the charging element output can be continuously adapted to provide sufficient capacitor charging while reducing or eliminating current spikes resulting from known systems. Embodiments of the invention are described in further detail with reference to FIGS. 6-30.

Referring to FIG. 6, one embodiment of the invention is a method 600 of adjusting or controlling the amount of energy delivered to a liquefaction handpiece or handpiece assembly (generally "handpiece"). Energy delivered to a handpiece adjusts the heating elements of the handpiece and thus, the temperature of the balanced salt solution (BSS). In step 610, the output of a charging element is monitored, e.g., at a voltage source, such as a capacitor, which provides energy to heat the handpiece heating elements. In step 620, the charging element is adjusted based on feedback from the voltage source so that in step 630, the adjusted charging element output is provided to the voltage source to adjust or control the amount of energy provided by the voltage source and delivered to the handpiece.

FIG. 7 illustrates a system 700 for adjusting energy delivered to a liquefaction handpiece according to one embodiment. The system 700 includes a power supply 710, an amplifier or charging element and regulator (generally "charging element" 720), a controller 730, a feedback loop 740 and a voltage source 750. According to one embodiment, the voltage source is a capacitor (generally, "capacitor 750").

The power supply 710 can be, for example, a 24 volt DC power supply or other suitable supply. The output 712 of the power supply 710 drives the charging element 720. The charging element 720 includes one or more inputs 722 and one or more outputs 724. Persons skilled in the art will appreciate then a charging element 720 can have different numbers of inputs and multiple outputs. Thus, the general illustration shown in FIG. 7 is not intended to be limiting, charging element 720

The voltage at the capacitor 750 at the output 724 of the charging element 720 is monitored. The monitored voltage is fed back 740 to the controller 730, which processes this data and generates an output 734. The controller output 734 is provided as an input 722 to the charging element 720, which adjusts the output 724 of the charging element 720. The feedback loop 740 can be used to dynamically and continuously adjust the charging element which, in turn, dynamically and continuously adjusts charging of the capacitor 750 and the amount of energy 754 provided by the capacitor 750 to the liquefaction handpiece 10. Adjusting the amount of energy provided to the liquefaction handpiece adjusts the heating elements and temperature of the BSS.

Figure 4:
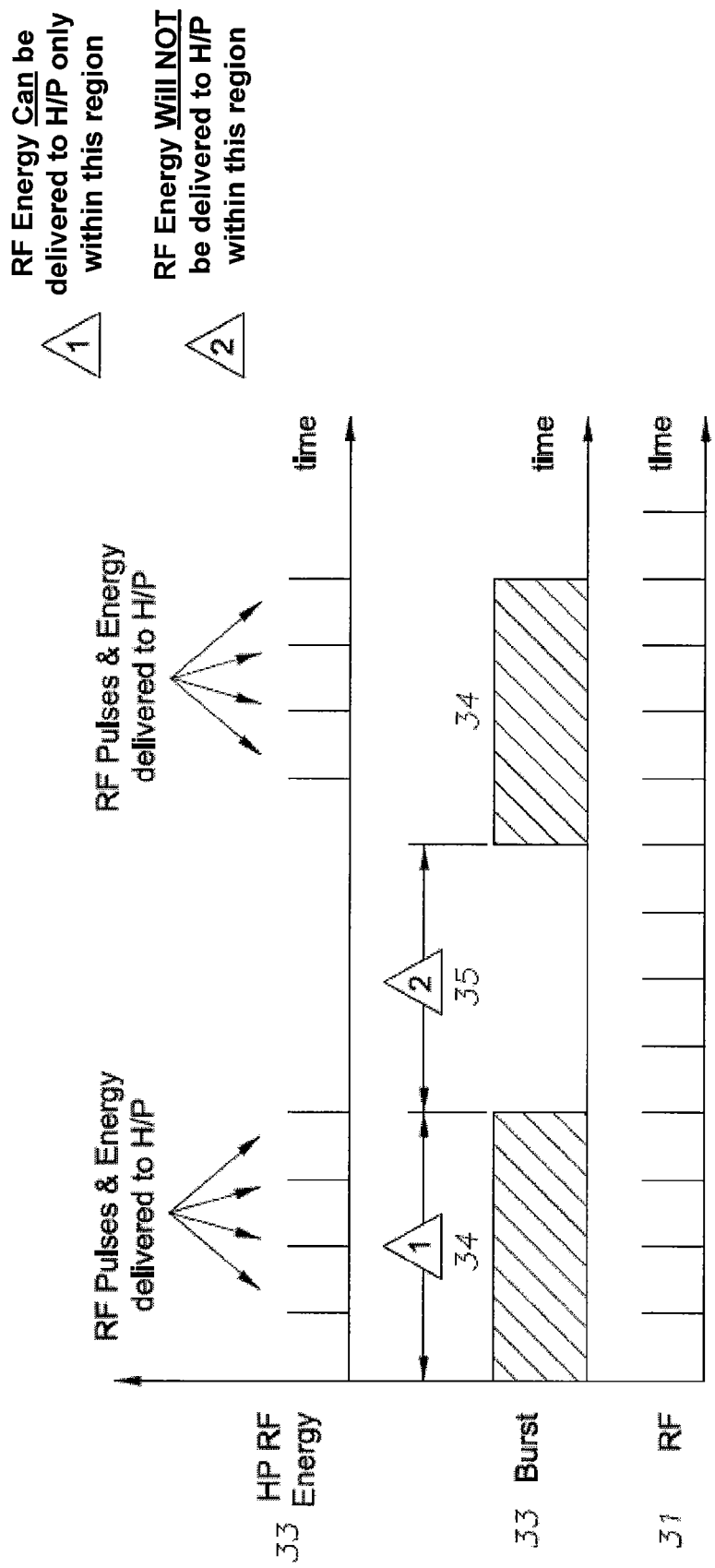
FIG. 4 illustrates known pulse patterns that are used for driving a liquefaction handpiece.
Figure 5:
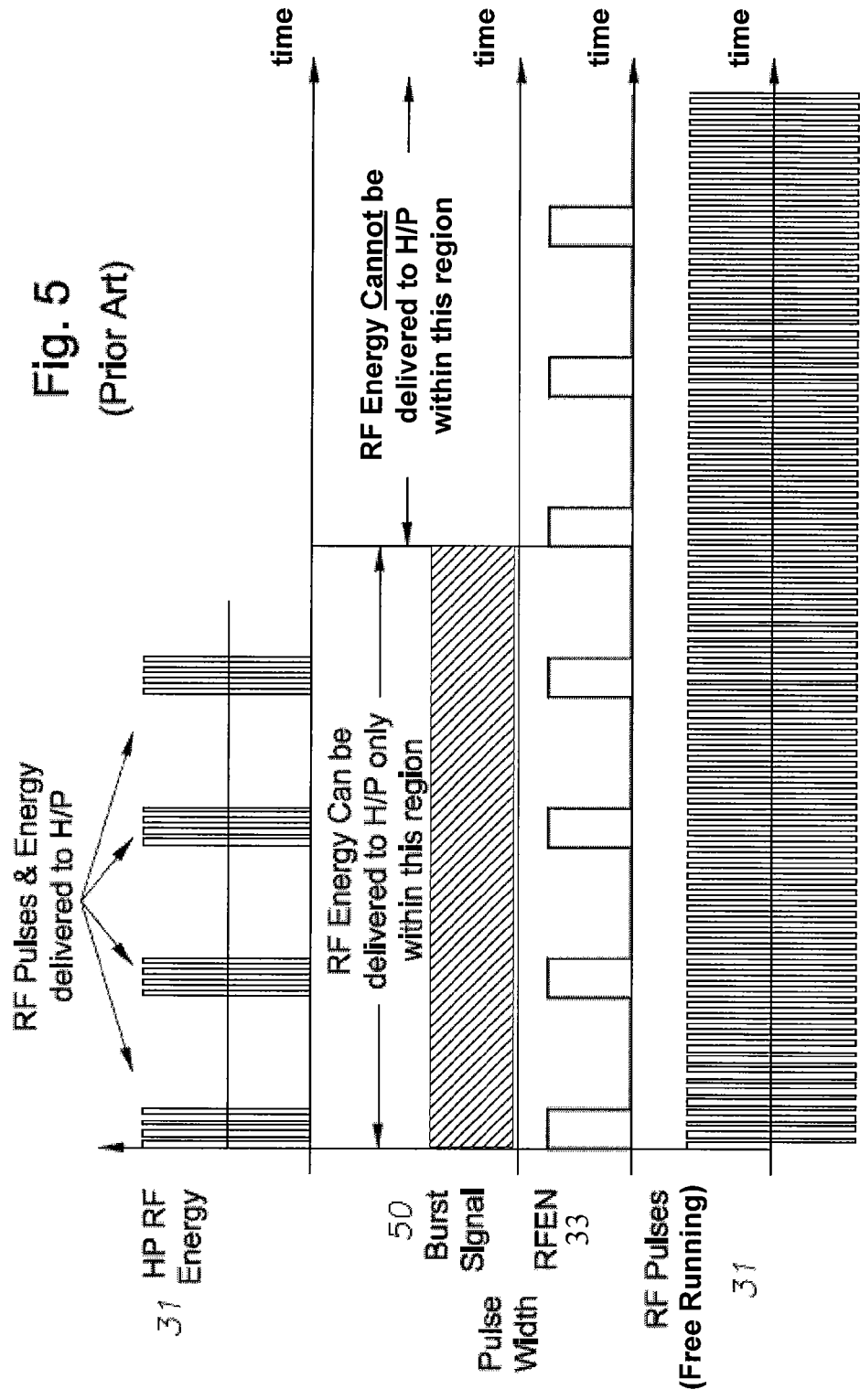
FIG. 5 further illustrates known pulse patterns that are used for driving a liquefaction handpiece.
Figure 8:
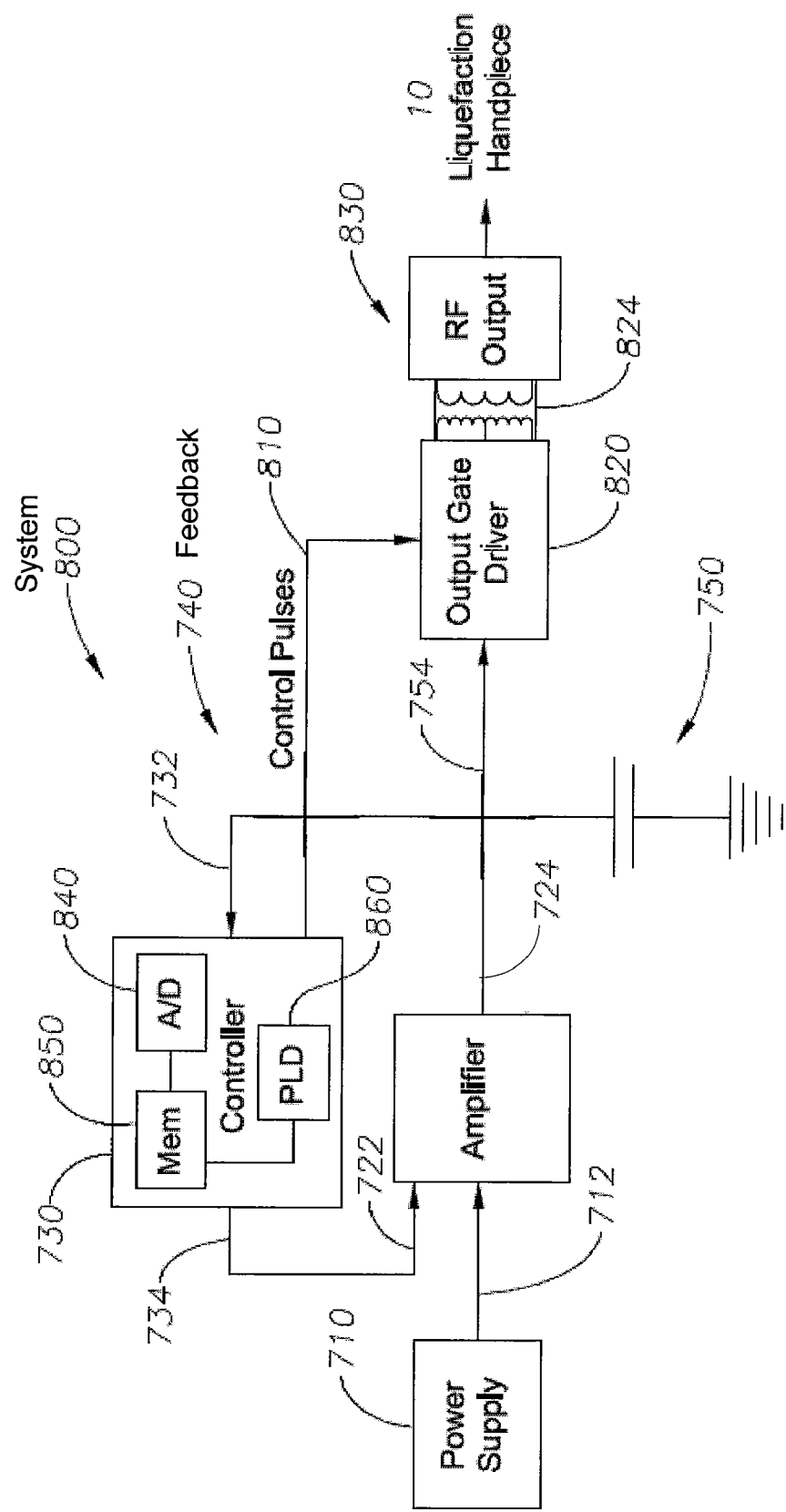
FIG. 8 is a more detailed block diagram of a system for adjusting the amount of energy delivered to a liquefaction handpiece using feedback according to one embodiment.

FIG. 8 illustrates a system 800 according to another embodiment of the invention. The system 800 includes a power supply 710, a charging element 720, a controller 730, a feedback loop 740, and a capacitor 750 as described with reference to FIG. 7. The output 724 of the charging element 720 is provided to the capacitor 750, which is charged by the output 724. FIG. 8 also illustrates control pulses 810 that are provided to an output gate driver or gating mechanism 820. Control pulses 810 can be generated by the controller 730 or an external pulse generator and are provided to the gate driver to generate an output 824 that defines active and inactive periods, e.g., pulses 33 shown in FIG. 4. Energy from the capacitor 750 is discharged through the gating mechanism 820 during the active period, through an RF output 830 and to the handpiece 10. The output 724 of the charging element 720 at the capacitor 750 is monitored and provided as an input 732 to the controller 730 as part of the feedback loop 740.

In the illustrated embodiment, the controller 730 includes an analog-to-digital (A/D) converter 840, a register, memory or other device 850 for holding or storing data, and a programmable logic device (generally "PLD") 860 or other suitable device. The voltage at the capacitor 750 is monitored and fed back 740 to an input 732 of the controller 730, i.e., to the A/D converter 840. The A/D converter 840 generates a digital value, e.g. a plurality of bits, corresponding to the received analog value. The digital value can be buffered in memory 850. Digital values corresponding to capacitor voltages at different times are provided to the PLD 860, which processes the digital values to determine how the charging element 720 should be adjusted.

Figure 9:
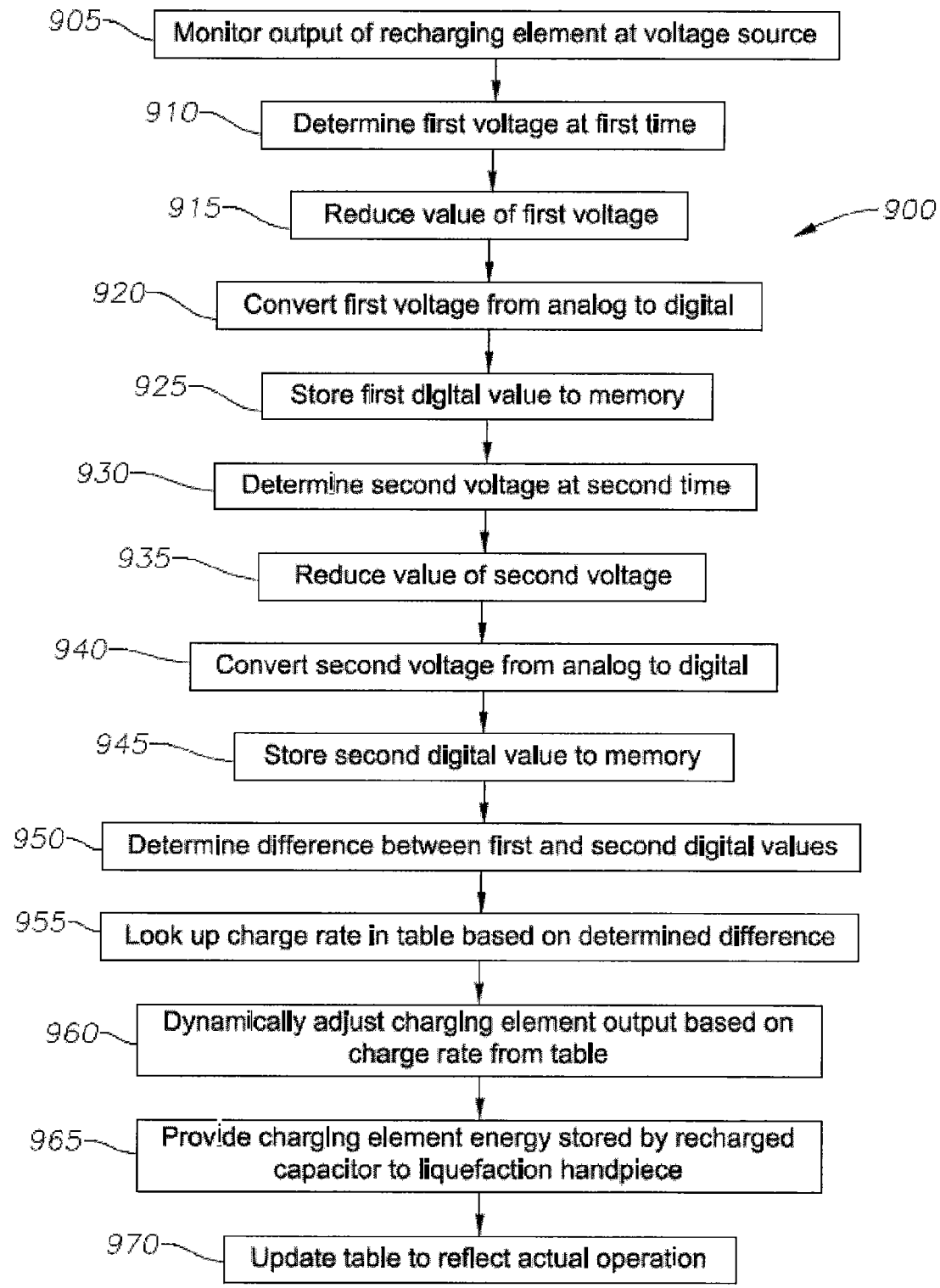
FIG. 9 is a flow chart illustrating a method for adjusting the amount of energy delivered to a liquefaction handpiece according to another embodiment.

More particularly, referring to FIG. 9, one embodiment of the invention is directed to a method 900 that includes monitoring the output of the recharging element at the capacitor or other voltage source in step 905. In step 910, a first voltage at the capacitor is determined at a first time. This voltage is a high voltage (HV), e.g., about 145 volts to about 165 volts, which can be reduced to a lower voltage that is suitable as an input to a controller. Thus, in step 915, the HV is reduced to a second, lower voltage, e.g., a TTL level voltage, which is suitable as an input to the controller. In step 920, the reduced first voltage is converted from analog to digital (e.g., a plurality of bits) by the A/D converter, and the digital value is stored to memory in step 925.

A second voltage of the output of the charging element at the voltage source is determined in step 930. The second voltage is reduced in step 935 and converted from analog to digital in step 940. The digital value corresponding to the second voltage can also be buffered to memory in step 945. Persons skilled in the art will appreciate that some; none or all of the digital values can be buffered to memory.

In step 950, the controller reads digital values from memory and determines the difference between first and second digital values that correspond to respective first and second voltages that were monitored at the capacitor at different times. In step 955, the controller looks up a rate at which the voltage of the charging element output increases over time based on the determined difference. This look-up can be based on a table that correlates determines differences to charge rates. In step 960, the charging element is adjusted based on the look-up, thereby causing the output of the charging element and recharging of the capacitor to be adjusted. In step 965, energy stored by the recharged capacitor is provided to the handpiece. This method can be repeated to compare second and third digital values, third and fourth digital values, and so on, for continuous and dynamic adjustment of the system.

In step 970, if necessary, the table values can be updated to reflect actual operation of the charging element to achieve desired charging of the capacitor. For example, for a given determined difference, the charge rate stored in the table can be increased or decreased based on actual system operation in the event that actual system operation varies from the corresponding the table entry. The updates can be repeated as necessary.

Figure 10A:
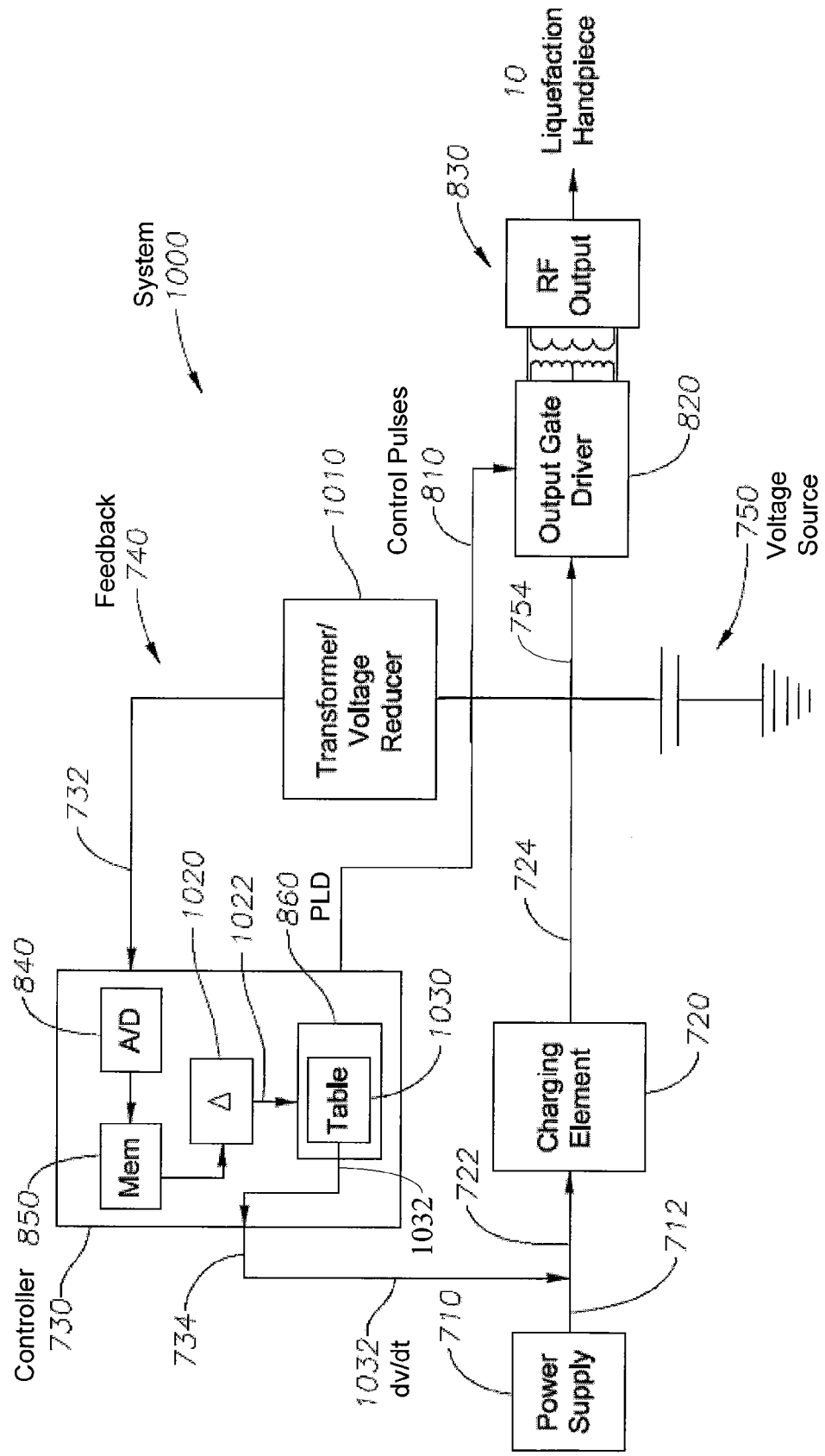
FIG. 10A is a block diagram of a system for adjusting the amount of energy delivered to a liquefaction handpiece using feedback according to another embodiment.

FIG. 10A illustrates a system 1000 that can be used to perform the method shown in FIG. 9 and other method embodiments. The system 1000 includes a power supply 710, a charging element 720, a controller 730, a feedback loop 740, and a voltage source 750, such as a capacitor, an output gate driver 820 and RF output 830, A/D converter 840, memory 850 and PLD 860, as discussed above. In the illustrated embodiment, the system 1000 includes a transformer or element 1010 that reduces voltage levels of the output 724 of the charging element 720 at the capacitor 750. For example, the transformer 1010 can reduce capacitor voltages of about 0 to about 200 volts to a lower level voltage of about 0 to 5 volts, e.g., TTL level voltages. The controller 730 also includes a processor or Arithmetic Logic Unit (ALU) 1020 that calculates differences between digital values buffered or stored in memory 850. The resulting difference calculations 1022 are provided to a PLD 860, which includes a table 1030. The table 1030 relates the difference values with corresponding rates at which the charging element output 724 increases over time. Thus, knowing the determined difference 1022, the table 1030 is used to determine a corresponding charge rate 1032 to dynamically adjust the output of the charging element 720 and to dynamically adjust charging of the capacitor 750.

Figure 10B:
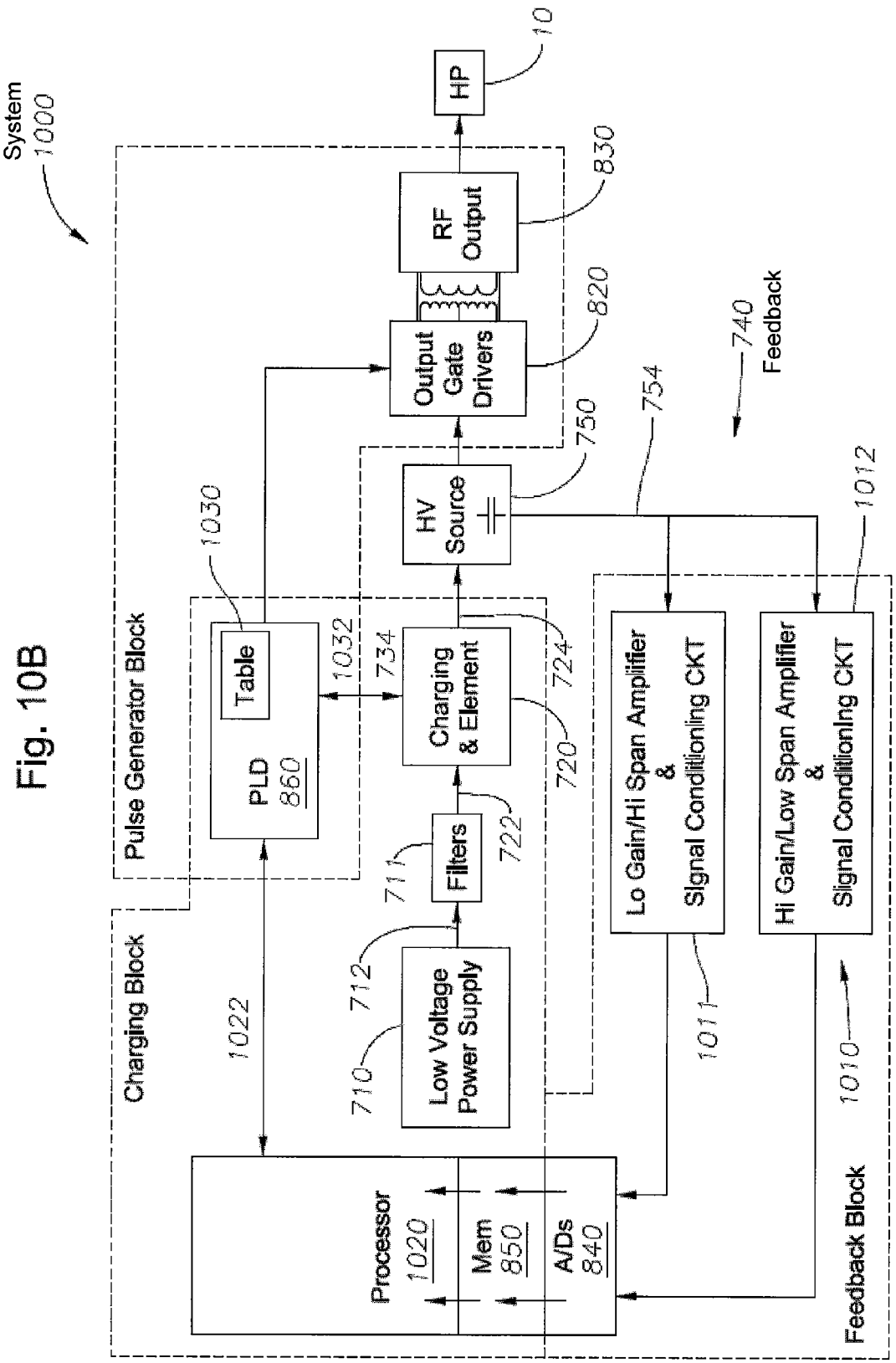
FIG. 10B is a block diagram of a system for adjusting the amount of energy delivered to a liquefaction handpiece using feedback according to another embodiment.

FIG. 10B further illustrates another implementation of the system 1000 shown in FIG. 10A. The system is shown as having three blocks—a charging mechanism block, a pulse generator block and a feedback block. The charging block includes the power supply 710 (and a filter 711 if necessary), a charging element 720, a PLD 860, memory 850 and a processor or ALU 1020. The output of the charging block 724 is used to charge a HV source 750, such as a capacitor. The output of the capacitor 750 is provided to a pulse generator block. The pulse generator block includes the output gate drivers 820 and RF output 830. In the illustrated embodiment, the PLD generates control pulses 810 that drive the gate drivers 820. Thus, the PLD can be considered to be part of the charging and pulse generator blocks in the illustrated embodiment.

The voltage at the capacitor 750 is monitored and fed back 740 through a transformer or voltage reducer 1010. In the illustrated embodiment, the transformer 1010 includes both a low gain/high span amplifier 1011 and a high gain/low span amplifier 1012. The reduced analog values provided to A/D converters 840 (shown as part of the feedback block in the illustrated embodiment), which provide digital values to memory 850. The digital values are provided from memory 850 to the processor 1020, which determines the difference between digital values. The determined difference is provided to the PLD, the output of which is fed back to the charging element to complete the feedback loop.

Figure 11:
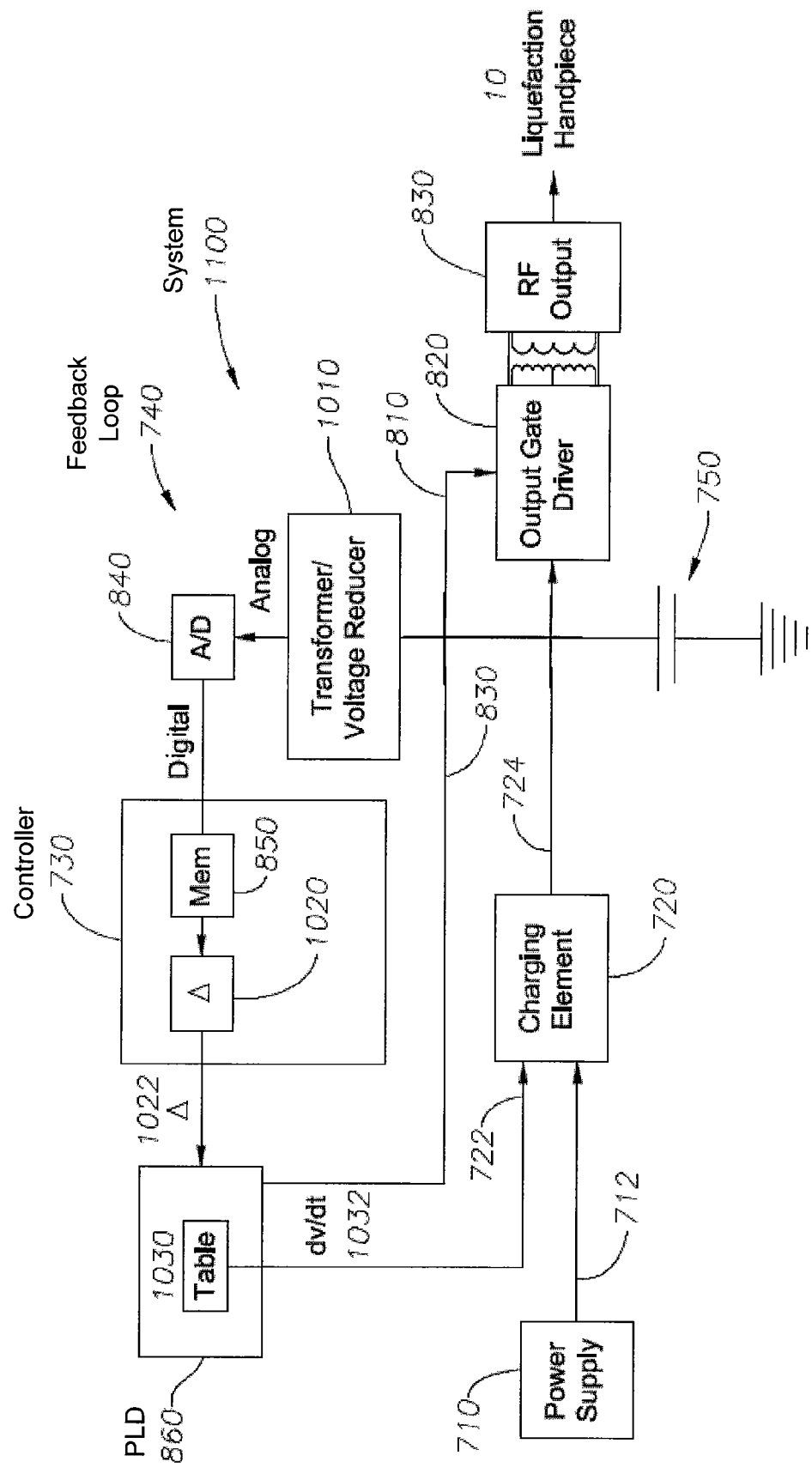
FIG. 11 illustrates an alternative configuration of the system shown in FIGS. 10A and 10B.

Persons skilled in the art will appreciate that the embodiments shown in FIGS. 10A and 10B are provided for purposes of illustration and explanation and that other elements can be utilized, and that certain elements can be part of different or multiple blocks. For example, FIG. 11 is similar to FIG. 10 except that in the embodiment shown in FIG. 10, the A/D converter 840 and the PLD 860 are components of the controller 730, whereas in FIG. 11, these the controller 730, A/D converter 840 and PLD 860 are separate components. Thus, embodiments can be implemented with various separate and combination hardware configurations, including the configurations shown in FIGS. 10A, 10B and 11. Reference is made to the controller 730 having an A/D converter 840 and PLD 860 for purposes of explanation and illustration, not limitation.

Figure 12:
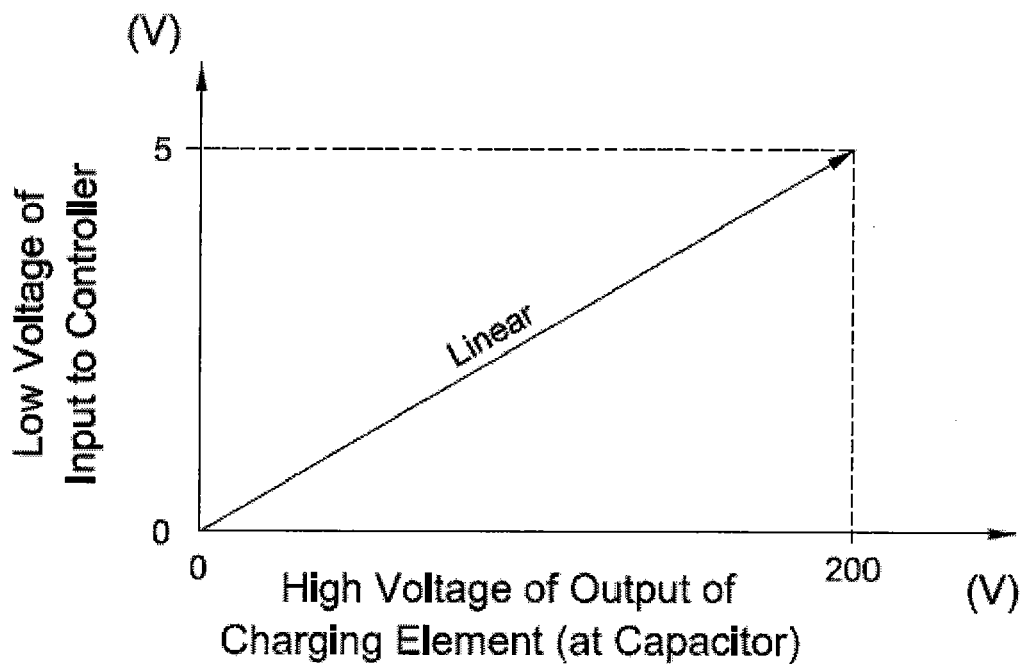
FIG. 12 illustrates the relationship between the voltage at the output of a charging element at a voltage source and an input of a controller.
Figure 13:
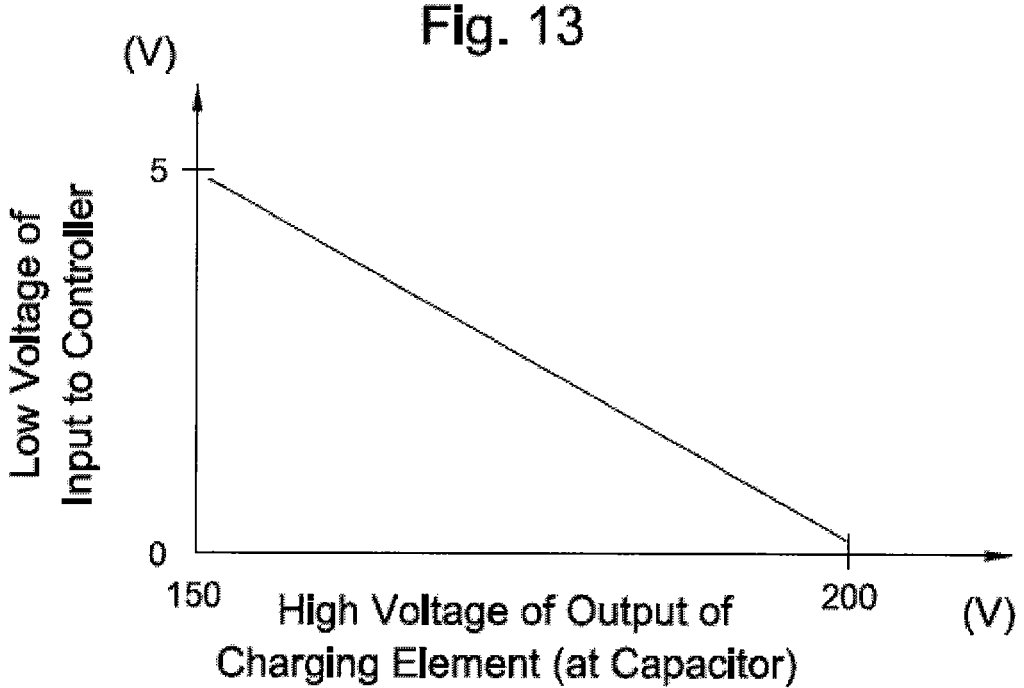
FIG. 13 further illustrates the relationship between the voltage at the output of a charging element at a voltage source and an input of a controller with higher resolution.

FIG. 12 is a chart showing how a voltage output at a level of 0-200 volts (at the capacitor 750) can be reduced to a level of 0-5 volts that is suitable for the controller 730. In the illustrated embodiment, the ratio of the high output voltage at the capacitor 750 to the lower voltage at the input 732 of the controller 730 is about 40/1 (200/5). It may be desirable to provide greater resolution for certain voltages. For example, as shown in FIG. 13, another output of the charging element 720 can monitor a voltage in the range of 150-200 volts (a range of 50 volts) to a corresponding voltage in the range of 0-5 volts, resulting in a ration of the high voltage range to lower voltage range being about 10/1 (50/5) rather than about 40/1 (200/5). In the illustrated embodiment, the slope of the line is negative (whereas in FIG. 12 it is positive).

Figure 14:
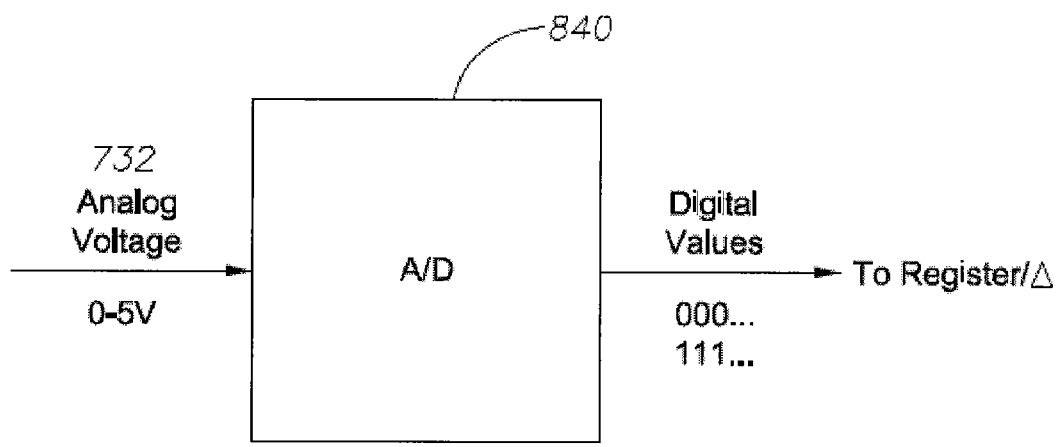
FIG. 14 illustrates an analog-to-digital (A/D) converter that accepts analog values and outputs digital values.
Figure 15:
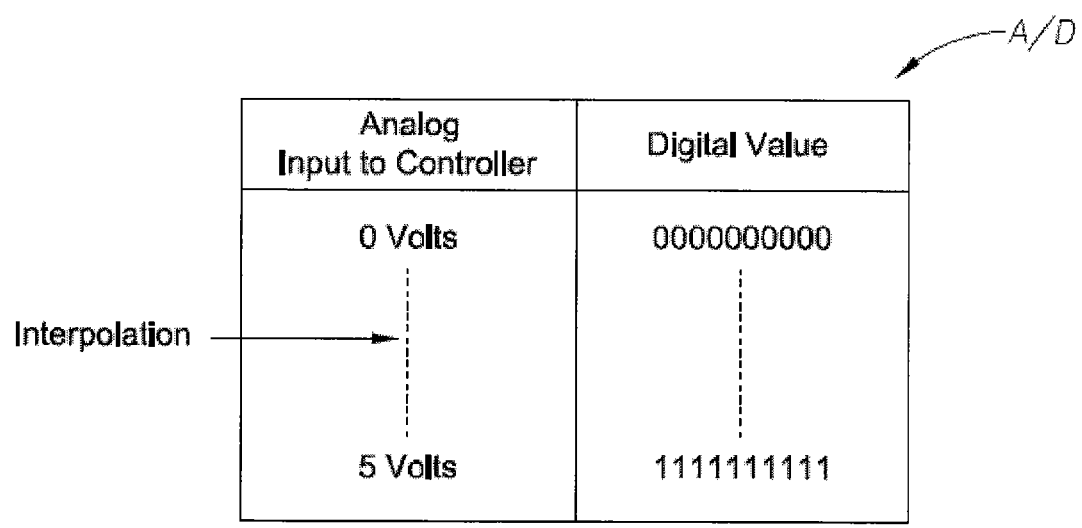
FIG. 15 illustrates analog input voltages based on the output from a charging element at a voltage source and corresponding digital representations or values.

FIGS. 14 and 15 illustrate in further detail how the reduced voltage at the input 732 of the controller 730 is converted into a corresponding digital value having one or more bits. The reduced analog voltage (0-5 volts) is provided to the A/D converter 840, which can be part of the controller 730 or a separate component. The A/D converter 840 receives the analog voltage and outputs a digital value 1400. Different numbers of bits can be used for different voltage ranges. Further, different numbers of bits can be used for different resolutions, i.e., a greater number of bits can be used to represent voltages with greater granularity.

Referring to FIG. 15, for example, the controller 730 or A/D converter 840 can include a table that represents a voltage of 0 volts using a plurality of "0" bits and a voltage of 5 volts is using a plurality of "1" bits. In the illustrated embodiment, each voltage is represented by 10 bits; however, other embodiments can utilize different numbers of bits and for different resolutions. A voltage between 0 and 5 volts can, according to one embodiment, be determined using interpolation between 0 volts (represented by a plurality of "0" bits) and 5 volts (represented by a plurality of "1" bits). Persons skilled in the art will appreciate that other methods besides interpolation can be used to determine digital values.

Figures 16, 17:
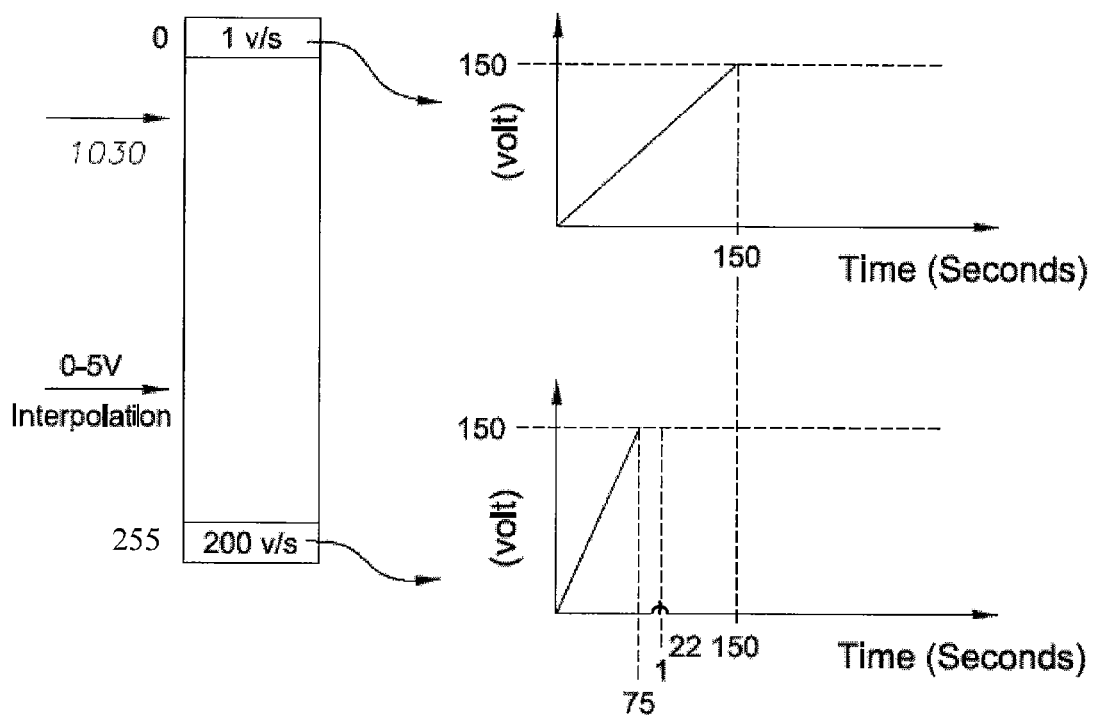
FIG. 16 illustrates a table that correlates differences between digital representations and rates of change according to one embodiment.
FIG. 17 illustrates different rates reflected in a table according to one embodiment.

Referring to FIG. 16, determined digital values 1400 are processed and the result is used to look up an operating parameter of the charging element 720 from a table. According to one embodiment, the difference (delta V) 1022 between two digital values 1040 is calculated, e.g. by an ALU or processor 1020. The table 1030 is accessed to determine a charging element operating parameter based on the determined difference. In the illustrated embodiment, the operating parameter is dv/dt 1032, or the change in the voltage of the charging element 720 over time, as shown in FIG. 17. In the illustrated embodiment, the lowest table value (0) corresponds to the slowest dv/dt 1032, and the highest table value (255) corresponds to the fastest dv/dt 1032. In the illustrated example, the table value (0) corresponds to a dv/dt value of 1 volt/second, and the table value (255) corresponds to a dv/dt value of 200 volts/second.

Persons skilled in the art will appreciate that that table 1030 can have various numbers of entries for different resolutions and for different devices that may require more or less entries. For example, rather than 256 entries as illustrated, a table can have 128 entries or 128 different dv/dt values 1032 corresponding to delta v values 1022. Further, the correlation of delta v values 1022 to dv/dt rates 1032 can vary. Additionally, the range of dv/dt values 1032 can vary. Thus, according to one embodiment, the dv/dt values 1032 in the table range from 1 v/s to 200 v/s, and other ranges can be used for different systems.

Figure 20:
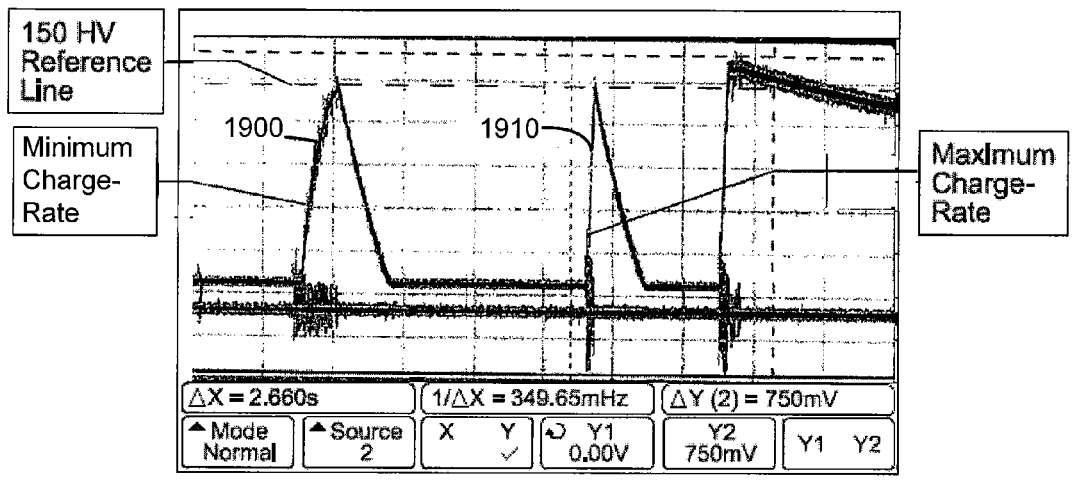
FIG. 20 is a display screen further illustrating profile pulses according to one embodiment.

FIGS. 18-20 illustrate a method 1800 for generating a table 1030 according to one embodiment. In step 1810, a pulse generator or PLD generates a first profile pulse. Referring to FIGS. 19 and 20, in the illustrated embodiment, the first profile pulse 1900 is the slowest dv/dt charge rate, and the charge rate is based on the time required for the pulse to reach an exemplary reference voltage of 150 volts. Referring again to FIG. 18, in step 1820, the table is populated with the data so that the minimum entry in the table corresponds to the minimum charge rate according to the first profile pulse. This is further illustrated in FIG. 19, which indicates that the PLD control value of "0" (table value of 0) represents the slowest charge rate dv/dt.

Referring again to FIG. 18, in step 1830, a second profile pulse is generated by a pulse generator or PLD. Referring to FIGS. 19 and 20, in the illustrated embodiment, the second profile pulse 1910 is the fastest charge rate dv/dt, and the charge rate is based on the time required for the pulse to reach the reference voltage of 150 volts. Referring again to FIG. 18, in step 1840, the table is populated with data from the second profile pulse so that the maximum entry in the table corresponds to the maximum charge rate according to the second profile pulse. This is further illustrated in FIG. 19, which indicates that the PLD control value of "255" (maximum table value of 255) represents the fastest charge rate dv/dt. Persons skilled in the art will appreciate that additional profile pulses can be generated. Additional profile pulses can populate intermediate portions of the table, and interpolation (or another suitable calculation method) can be used to determine dv/dt values between selected table values generated by profile pulses.

Figure 21:
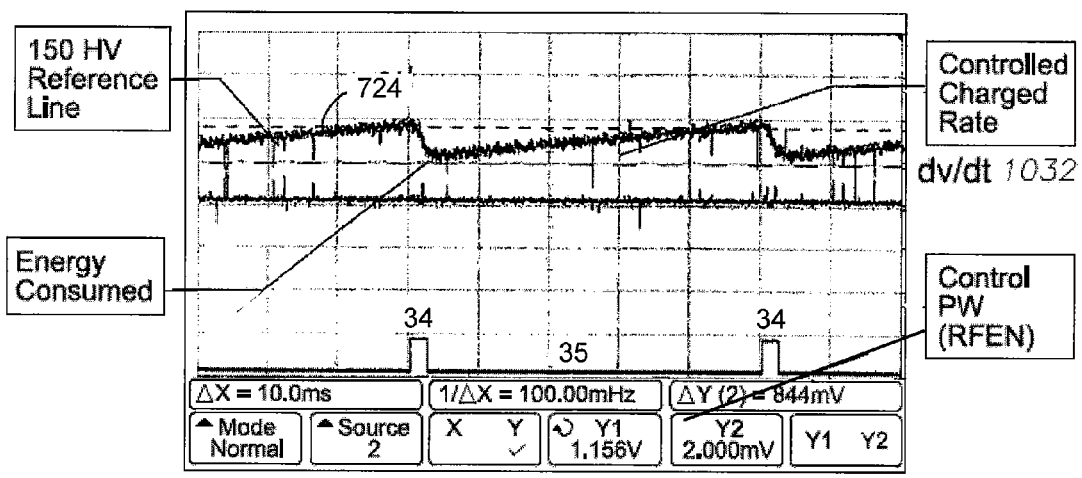
FIG. 21 illustrates a control pulse triggering discharging of energy stored by a capacitor to a liquefaction handpiece and recharging the capacitor according to one embodiment.

The table 1030 in the PLD 860 is used to identify a particular charging element operating parameters, such as dv/dt 1032, based on the determined difference 1022 between digital values based on feedback from the charging element 720, to ensure that the output 724 of the charging element 720 is dynamically adjusted to achieve the desired charging of the capacitor 750. Referring to FIG. 21, the output 724 of the charging element 720 rises and falls based on the pulses (RFEN), which trigger discharging energy stored by the capacitor 750 to the handpiece 10 during active pulse periods 34. The desired operation of the system is to have the voltage of the charging element increase sufficiently quickly (but without causing current spikes while placing reduced or minimum burden on system power resources) so that the voltage at the capacitor 750 reaches the reference voltage (150V in this example), before the next pulse 34 recharge element output 724. This feedback driven charging ensures that the capacitor 750 is sufficiently charged (but not too quickly or too slowly) so that the handpiece 10 receives the correct amount of energy during each pulse 34.

Figure 22:
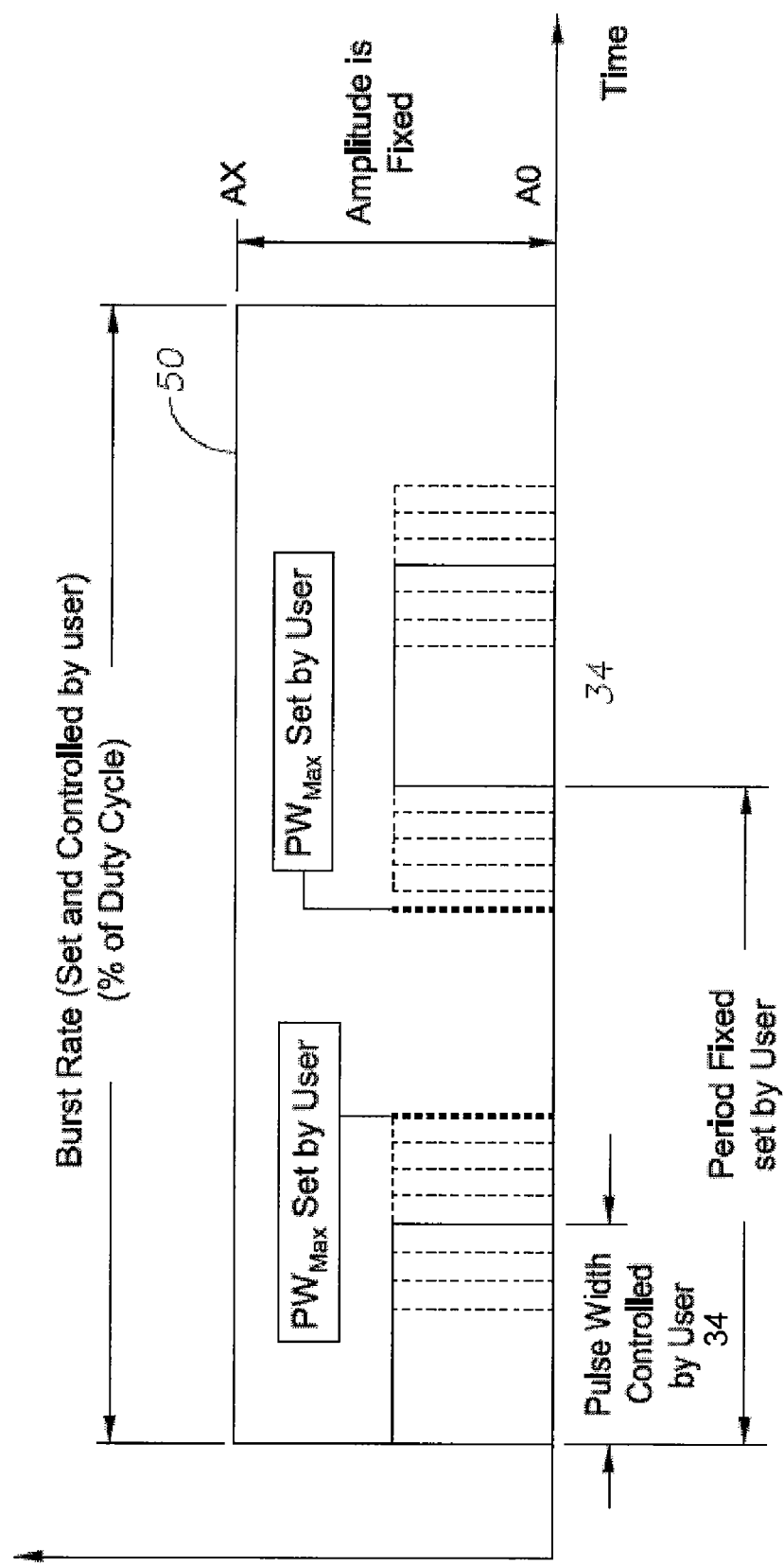
FIG. 22 illustrates control pulse parameters for use with various embodiments.

Referring to FIG. 22, in use, a surgeon can set a burst period 50 during which control pulses 34 trigger providing energy to the handpiece 10, e.g. from discharging the capacitor 750 that is recharged by the charging element recharge element output 724. The duration of the control pulses 34 can be selected by the surgeon. The surgeon can also set the period of time between the beginning of a first pulse and the beginning of a second pulse. Individual pulse durations can be the same, or they can be different, as shown in FIG. 23.

Figure 23:
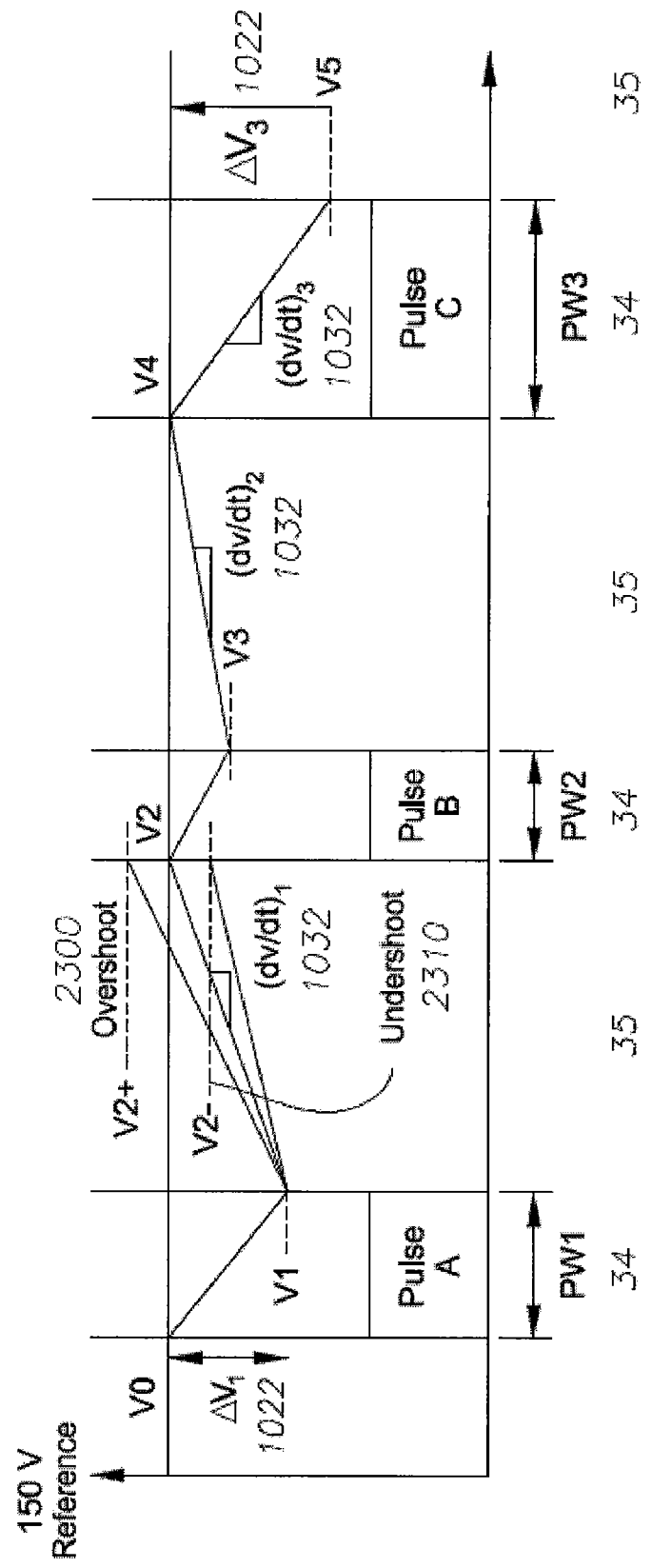
FIG. 23 illustrates examples of recharge overshoot and undershoot relative to a reference voltage.

Referring to FIG. 23, HV values from the capacitor 750 at the output of the charging element capacitor 750 are measured immediately before (or at the beginning) of a control pulse 34, and at the end of a control pulse 34. Thus, energy is provided to the handpiece during PW1, during PW2 and during PW3. After each pulse, the capacitor 750 is recharged by the charging element recharge element output 724 until the next control pulse 34 arrives to discharge the capacitor 750 and provide energy to the handpiece 10.

As shown in FIG. 23, the amount of energy provided to the handpiece during each "energy release" can vary. For example, beginning at "time 0", the voltage V0 at the capacitor 750 is at the reference voltage, which is 150V in this example. Control pulse A, having a duration or width PW1, triggers the capacitor 750 to be discharged, resulting in energy stored by the capacitor 750 to be provided as an input to the liquefaction handpiece 10 which, in turn, causes the voltage at the capacitor to be reduced from V0 at the beginning of PW1 to V1 at the end of PW1. The voltage reduction occurring during PW1 is indicated by delta V1.

At the end of PW1, the capacitor 750 ceases providing energy to the handpiece and is recharged. Ideally, the capacitor 750 is recharged to the reference voltage, or 150V or V2. The rate at which the capacitor first recharges is identified as (dv/dt)1. In practice however, the capacitor 750 may not be recharged according to the intended design due to, for example, variations in the charging element components. Thus, the capacitor 750 may recharge beyond the reference voltage to voltage V2+, otherwise referred to as overshoot 2300, or the capacitor 750 may recharge below the reference voltage to V2−, otherwise referred to as undershoot 2310.

Control pulse B, having a duration or width PW2, triggers the capacitor 750 to be discharged a second time, resulting in energy stored by the capacitor 750 to be provided as an input to the liquefaction handpiece 10 which, in turn, causes the voltage at the capacitor 750 to be reduced from V2 at the beginning of PW2 to V3 at the end of PW2. The voltage reduction occurring during PW2 is indicated by delta V2. In the illustrated example, the voltage drops during the PW1 and PW2 are different. At the end of PW2, the capacitor 750 ceases providing energy to the handpiece 10 (if any stored charge remains) and is recharged. Ideally, the capacitor 750 is recharged to the reference voltage, or 150V or V4. The rate at which the capacitor 750 recharges the second time is identified as (dv/dt)2 1032. In practice however, the capacitor 750 may not be recharged according to the intended design. Similarly, control pulse C, having a duration or width PW3, triggers the capacitor 750 to be discharged a third time, resulting in energy stored by the capacitor 750 to be provided as an input to the liquefaction handpiece 10 which, in turn, causes the voltage at the capacitor 750 to be reduced from V4 at the beginning of PW3 to V5 at the end of PW3. The voltage reduction occurring during PW3 is indicated by delta V3. In the illustrated example, the voltage drops during PW1, PW2 and PW3 are different. At the end of PW3, the capacitor 750 ceases providing energy to the handpiece 10 (if any stored charge remains) and is recharged again. The energy release and recharge sequence continues using additional control pulses, energy releases and recharging, as discussed above.

Figure 24:
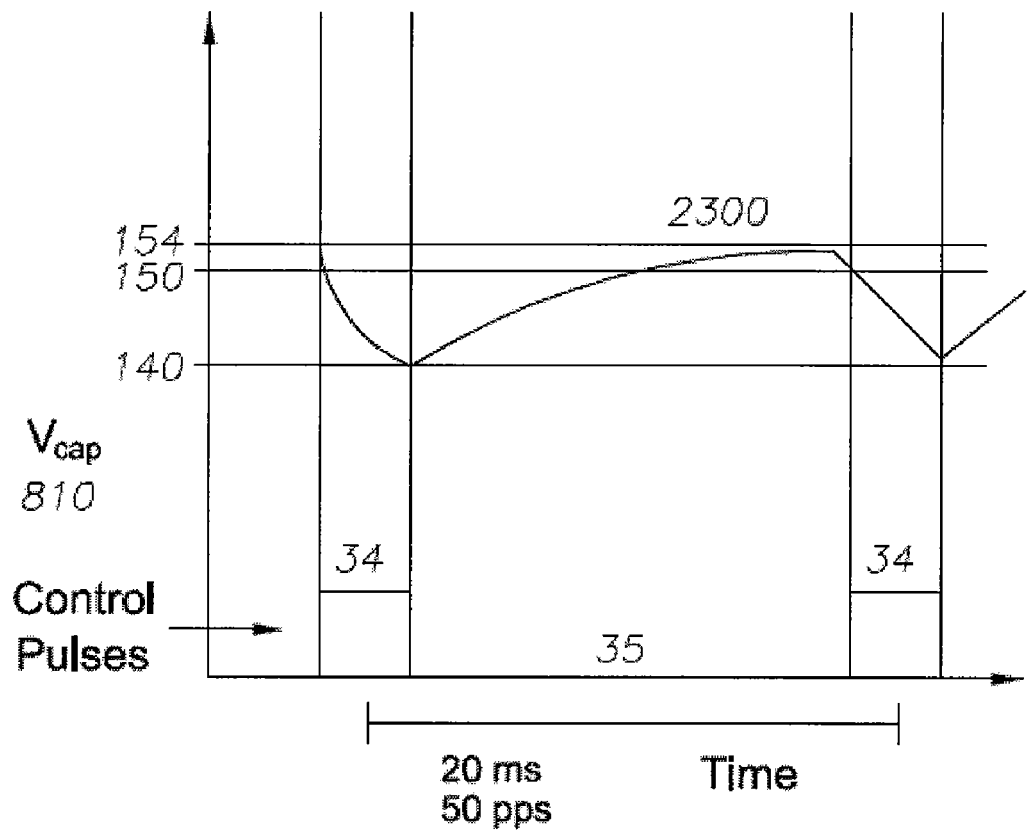
FIG. 24 further illustrates overshoot.
Figure 25:
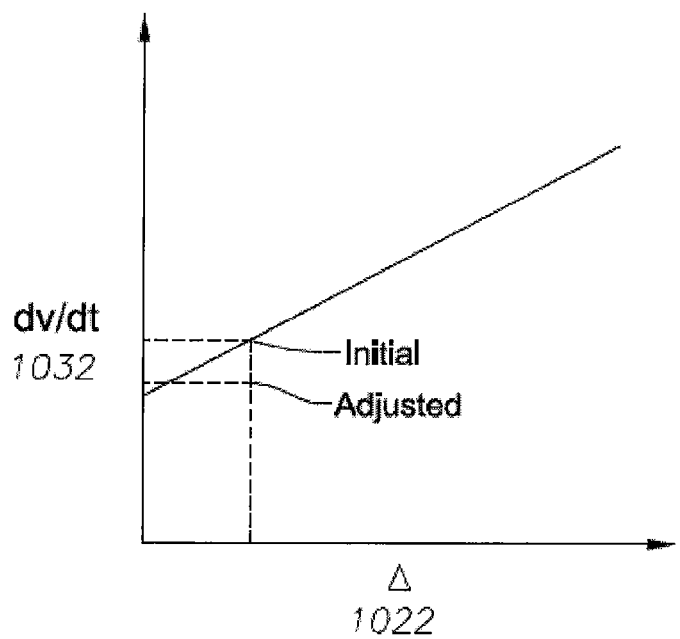
FIG. 25 illustrates adjusting a recharging element to compensate for overshoot using feedback according to one embodiment.

FIGS. 24-29 illustrate how the table 1030 can be adjusted based on feedback from the recharge element output 724 in order to prevent overshoot 2300 and undershoot 2310. FIG. 24 illustrates an example of overshoot 2300 during which a delta value 1022 of the table 1030 initially determined that the corresponding dv/dt value 1032 should have been "X" so that the capacitor 750 recharged to 150 volts before the next control pulse 34, but the charging element 720 actually overcharged the capacitor 750 to 154 volts. Thus, this is an overshoot 2300 of four volts. Referring to FIG. 25, the dv/dt value 1032 in the table 1030 corresponding to that particular delta value 1022 can be adjusted downwardly to compensate for the overshoot 2300 so that the next time that delta value 1022 is called, the reduced dv/dt value 1032 will be provided as an input 722 to the charging element 720, and the recharge element output 724 will result in the capacitor 750 being recharged to the reference voltage. If the capacitor 750 is not charged to the reference voltage, further adjustments can be made to compensate for any subsequent overshoot or undershoot.

Figure 26:
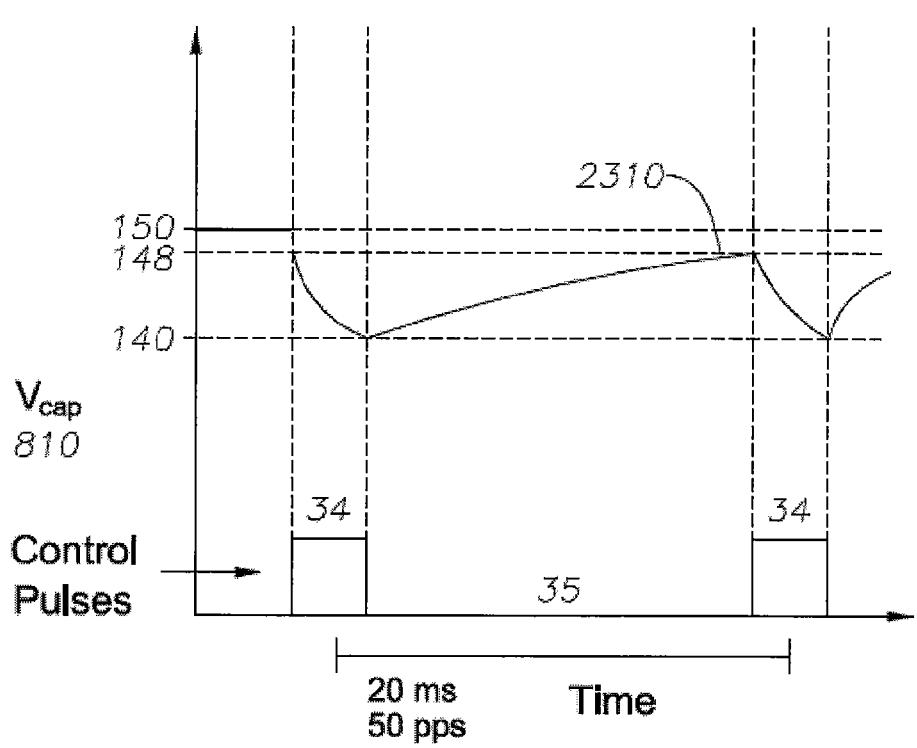
FIG. 26 illustrates an example of undershoot.
Figures 27, 28:
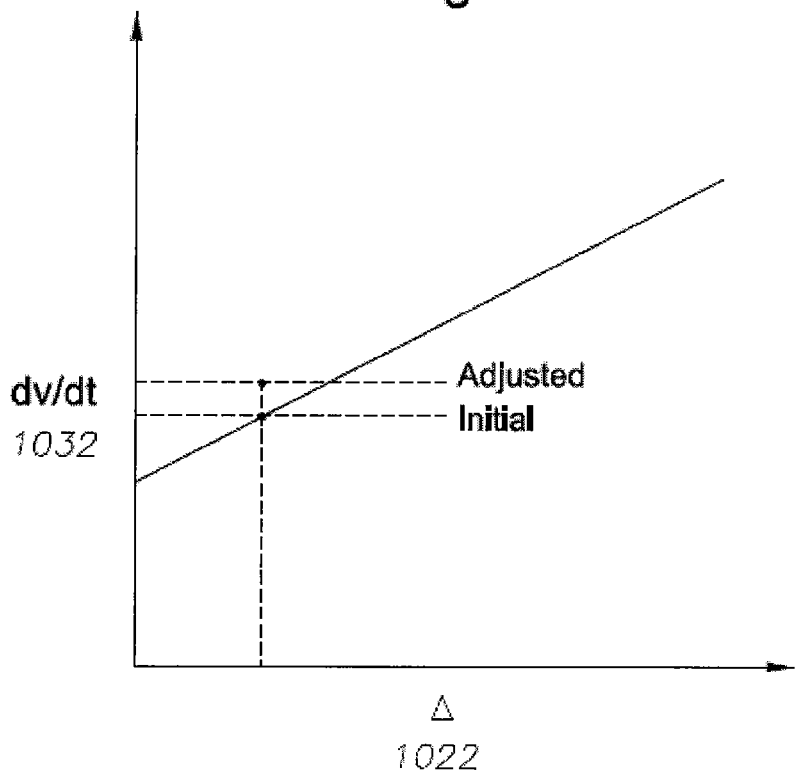
FIG. 27 illustrates adjusting a recharging element to compensate for undershoot using feedback according to one embodiment.
FIG. 28 illustrates a table that relates determined differences between digital values and charge rates according to one embodiment.

Similarly, FIG. 26 illustrates an example of undershoot 2310 during which a delta value 1022 of the table 1030 initially determined that the corresponding dv/dt value 1032 should have been "X" so that the capacitor 750 recharged to 150 volts before the next control pulse 34, but the charging element 720 actually undercharged the capacitor 750 to 148 volts. Thus, this is an undershoot 2310 of two volts. Referring to FIG. 27, the dv/dt value 1032 in the table 1030 corresponding to that particular delta value 1032 can be adjusted upwardly to compensate for the undershoot 2310 so that the next time that delta value 1022 is called, the increased dv/dt value 1032 will be provided as an input 722 to the charging element 720, and the recharge element output 724 will result in the capacitor 750 being recharged to the reference voltage. Any subsequent overshoot or undershoot can be adjusted further with additional feedback iterations as necessary.

Figure 29:
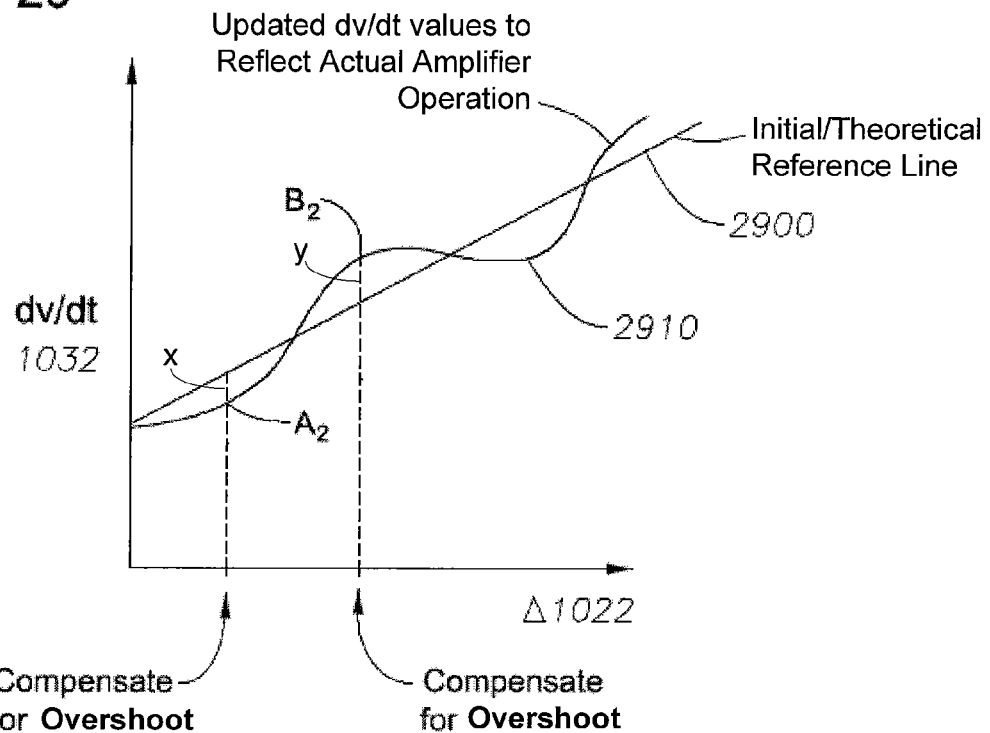
FIG. 29 illustrates dynamically updating table entries to reflect actual system operation according to one embodiment.
Figure 30:
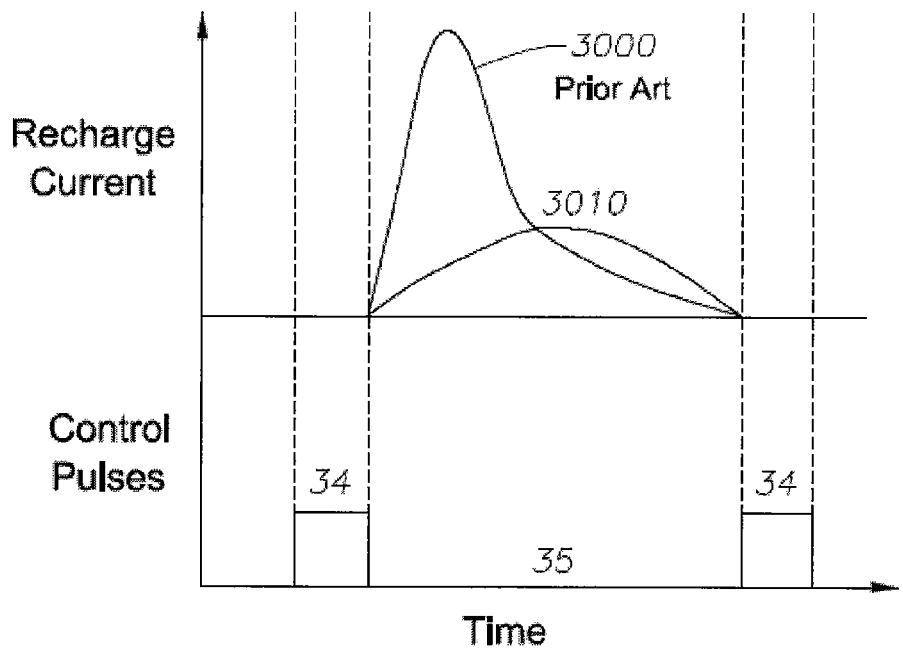
FIG. 30 illustrates advantages of embodiments of the invention relative to known systems that generate current spikes.

Referring to FIG. 28, the original table 1030 can be dynamically updated to reflect actual operation of the charging element 720. The table 1030 includes updated or adjusted dv/dt values 1032 to compensate for any overshoot 2300 and undershoot 2310 by respectively reducing and increasing the dv/dt value 1032 based on a determined voltage difference 1022 determined from feedback from the charging element 720. Thus, referring to FIG. 29, expected charging element operation is indicated by a linear line 2900, and deviations from this model that reflects actual charging element 720 operation is shown by line 2910. Line 2910 represents dv/dt values 1032 that correspond to different voltage differences and can form various linear and non-linear sections or relationships. Persons skilled in the art will appreciate that the exemplary graph shown in FIG. 29 is provided for purposes of illustration, not limitation, since the charging element 720 may operate as intended, have different numbers and durations of overshoot instances, and have different numbers and durations of undershoot instances.

Embodiments provide a number of improvements over known systems that do not utilize dynamic feedback. For example, referring to FIG. 30, known systems that are configured to charge a capacitor at the maximum charging rate typically generate current spikes 3000, which can result in unnecessary consumption of power and more complicated circuit designs that must accommodate these surges. Embodiments improve upon known systems by reducing or eliminating the "spike" effect by providing a more moderate increase in current 3010 and power.

Although references have been made in the foregoing description to various embodiments, persons of skilled in the art will recognize that insubstantial modifications, alterations, and substitutions can be made to the described embodiments without departing from the scope of embodiments. For example, certain system components can be separate components or part of a controller, and certain system components can be part of a single assembly or distributed among multiple components.

Further, the output of the charging element at the voltage source can be sampled at different frequencies and for various time periods to provide different amounts of feedback as necessary. Various numbers, durations and frequencies of control pulses can be utilized to trigger providing energy to the handpiece. Additionally, the A/D converter can represent analog voltages as digital values having different numbers of bits to provide different resolutions. Delta values can be calculated based on digital values obtained at various times and based on digital values have various numbers of bits.

Additionally, the table used to provide feedback to the charging element can include various numbers of entries to provide different degrees of feedback. Thus, the table can have 128 or 256 entries, or other numbers of entries as needed. Table updates can be performed at various times. Monitoring the output, determining digital values, determining delta values, determining dv/dt values, and providing feedback to the charging element input can be performed periodically or non-periodically.

What is claimed is:

1. A system for controlling an amount of energy delivered to a handpiece of a surgical system, comprising:
a power supply;
a charging element, wherein the power supply is configured to drive the charging element;
a voltage source at an output of the charging element, wherein a voltage of the voltage source is monitored; and
a controller,
wherein data from monitoring the voltage source is provided to the controller,
wherein the controller is configured to generate an output that is provided to the charging element to dynamically adjust the charging element output, and
wherein the amount of energy provided by the voltage source as an input to the handpiece is dynamically adjusted based on the adjusted charging element output;
wherein the output of the controller compensates for undershoot, wherein undershoot occurs when the voltage of the charging element output is less than a predetermined voltage after a predetermined time.

2. The system of claim 1, further comprising a pulse generator that outputs a control pulse, wherein energy stored by the voltage source is provided as the input to the handpiece in response to the control pulse.

3. The system of claim 2, wherein the pulse generator is configured to output a plurality of control pulses, and wherein energy stored by the voltage source is provided as the input to the handpiece in response to each control pulse, wherein the voltage source is recharged between control pulses, and wherein a rate at which the voltage source is recharged is determined by the adjusted output of the charging element.

4. The system of claim 3, wherein the rate at which the voltage of the adjusted charging element output increases is determined so that the voltage source is recharged to a predetermined level before the next control pulse.

5. The system of claim 4, wherein the voltage source is fully recharged before the next control pulse.

6. The system of claim 1, further comprising a transformer connected between the voltage source and an input of the controller, wherein the transformer is configured to receive monitored data from the voltage source as an input and generates an output that is provided as an input to the controller.

7. The system of claim 6, wherein the transformer is configured to reduce a level of the monitored data from a first level to a second level.

8. The system of claim 7, wherein the transformer is configured to reduce the level of the monitored data from about 0-200 volts to about 0-5 volts.

9. The system of claim 6, wherein the controller is configured to convert the monitored data from an analog value to a digital value.

10. The system of claim 9, wherein the controller is configured to determine a difference between a first digital value and a second digital value, the charging element output being dynamically adjusted based on the determined difference.

11. The system of claim 1,
wherein the controller is configured to receive a first input of a first monitored voltage at a first time,
wherein the controller is configured to receive a second input of a second monitored voltage at a second time,
wherein the controller is configured to determine a difference between the first and second monitored voltages and generate an output based on the determined difference that dynamically adjusts the output of the charging element.

12. The system of claim 11, wherein the controller is configured to determine from a table a rate at which the voltage of the charging element output increases over time based on the determined difference, and wherein the table identifies determined differences between digital values and corresponding rates at which a voltage of the charging element output increases.

13. The system of claim 12, wherein the table is automatically generated at power up of the system.

14. The system of claim 12, wherein the controller is configured to automatically update the table based on feedback from the charging element output.

15. The system of claim 1,
wherein data from monitoring the voltage source is monitored to determine a first voltage value at a first time and a second voltage value at a second time,
wherein the controller is configured to convert the first voltage to a first digital value and the second voltage to a second digital value, determine a difference between the first and second digital voltage values, and perform a look-up in a table that correlates determined differences and outputs of the charging element,
wherein the charging element output is dynamically adjusted based on the look-up performed by the controller, and the amount of energy provided by the voltage source as an input to the handpiece is dynamically adjusted based on the adjusted charging element output.

16. The system of claim 15, wherein the controller includes a micro-processor and a programmable logic device, wherein the table is stored in the programmable logic device.

17. The system of claim 15, wherein the table is automatically generated at power up of the system.

18. The system of claim 1, further comprising:
a memory configured to store a table that correlates values representing a difference between monitored voltages and dv/dt, wherein dv/dt is a rate of change of the voltage of the output of the charging element, wherein a minimum value in the table is based on a first profile pulse and a time for the first profile pulse to reach a predetermined voltage, wherein a maximum value in the table is based on a second profile pulse and a time for the second profile pulse to reach the predetermined voltage, the second profile pulse reaching the predetermined threshold faster than the first profile pulse;
wherein the controller is configured to receive as inputs from the voltage source a first voltage at a first time and a second voltage at a second time, convert the first voltage to a first digital value and the second voltage to a second digital value, determine a difference between the first and second digital voltage values, and perform a look-up in the table to determine dv/dt based on the determined difference;
wherein the charging element output is dynamically adjusted based on the look-up performed by the controller, and the amount of energy provided by the voltage source as the input to the handpiece is dynamically adjusted based on the adjusted charging element output.

19. The system of claim 18, wherein the table is automatically updated based on feedback from the voltage source.

20. The system of claim 1, wherein monitoring the voltage source and providing the controller data from monitoring the voltage source comprises the controller detecting a voltage of the voltage source.

21. A system for controlling an amount of energy delivered to a handpiece of a surgical system, comprising:
a power supply;
a charging element, wherein the power supply is configured to drive the charging element;
a voltage source at an output of the charging element, wherein a voltage of the voltage source is monitored; and
a controller,
wherein data from monitoring the voltage source is provided to the controller,
wherein the controller is configured to generate an output that is provided to the charging element to dynamically adjust the charging element output, and
wherein the amount of energy provided by the voltage source as an input to the handpiece is dynamically adjusted based on the adjusted charging element output;
wherein the output of the controller compensates for overshoot, wherein overshoot occurs when the voltage of the charging element output is greater than a predetermined voltage after a predetermined time.

22. The system of claim 21, further comprising a pulse generator that outputs a control pulse, wherein energy stored by the voltage source is provided as the input to the handpiece in response to the control pulse.

23. The system of claim 22, wherein the pulse generator is configured to output a plurality of control pulses, and wherein energy stored by the voltage source is provided as the input to the handpiece in response to each control pulse, wherein the voltage source is recharged between control pulses, and wherein a rate at which the voltage source is recharged is determined by the adjusted output of the charging element.

24. The system of claim 23, wherein the rate at which the voltage of the adjusted charging element output increases is determined so that the voltage source is recharged to a predetermined level before the next control pulse.

25. The system of claim 24, wherein the voltage source is fully recharged before the next control pulse.

26. The system of claim 21, further comprising a transformer connected between the voltage source and an input of the controller, wherein the transformer is configured to receive monitored data from the voltage source as an input and generates an output that is provided as an input to the controller.

27. The system of claim 26, wherein the transformer is configured to reduce a level of the monitored data from a first level to a second level.

28. The system of claim 27, wherein the transformer is configured to reduce the level of the monitored data from about 0-200 volts to about 0-5 volts.

29. The system of claim 26, wherein the controller is configured to convert the monitored data from an analog value to a digital value.

30. The system of claim 29, wherein the controller is configured to determine a difference between a first digital value and a second digital value, the charging element output being dynamically adjusted based on the determined difference.

31. The system of claim 21,
wherein the controller is configured to receive a first input of a first monitored voltage at a first time,
wherein the controller is configured to receive a second input of a second monitored voltage at a second time,
wherein the controller is configured to determine a difference between the first and second monitored voltages and generate an output based on the determined difference that dynamically adjusts the output of the charging element.

32. The system of claim 31, wherein the controller is configured to determine from a table a rate at which the voltage of the charging element output increases over time based on the determined difference, and wherein the table identifies determined differences between digital values and corresponding rates at which a voltage of the charging element output increases.

33. The system of claim 32, wherein the table is automatically generated at power up of the system.

34. The system of claim 32, wherein the controller is configured to automatically update the table based on feedback from the charging element output.

35. The system of claim 21,
wherein data from monitoring the voltage source is monitored to determine a first voltage value at a first time and a second voltage value at a second time,
wherein the controller is configured to convert the first voltage to a first digital value and the second voltage to a second digital value, determine a difference between the first and second digital voltage values, and perform a look-up in a table that correlates determined differences and outputs of the charging element,
wherein the charging element output is dynamically adjusted based on the look-up performed by the controller, and the amount of energy provided by the voltage source as an input to the handpiece is dynamically adjusted based on the adjusted charging element output.

36. The system of claim 35, wherein the controller includes a micro-processor and a programmable logic device, wherein the table is stored in the programmable logic device.

37. The system of claim 35, wherein the table is automatically generated at power up of the system.

38. The system of claim 21, further comprising:
a memory configured to store a table that correlates values representing a difference between monitored voltages and dv/dt, wherein dv/dt is a rate of change of the voltage of the output of the charging element, wherein a minimum value in the table is based on a first profile pulse and a time for the first profile pulse to reach a predetermined voltage, wherein a maximum value in the table is based on a second profile pulse and a time for the second profile pulse to reach the predetermined voltage, the second profile pulse reaching the predetermined threshold faster than the first profile pulse;
wherein the controller is configured to receive as inputs from the voltage source a first voltage at a first time and a second voltage at a second time, convert the first voltage to a first digital value and the second voltage to a second digital value, determine a difference between the first and second digital voltage values, and perform a look-up in the table to determine dv/dt based on the determined difference;
wherein the charging element output is dynamically adjusted based on the look-up performed by the controller, and the amount of energy provided by the voltage source as the input to the handpiece is dynamically adjusted based on the adjusted charging element output.

39. The system of claim 38, wherein the table is automatically updated based on feedback from the voltage source.

40. The system of claim 21, wherein monitoring the voltage source and providing the controller data from monitoring the voltage source comprises the controller detecting a voltage of the voltage source.

41. A system for controlling an amount of energy delivered to a handpiece of a surgical system, comprising:
a power supply;
a charging element, wherein the power supply is configured to drive the charging element;
a voltage source at an output of the charging element, wherein the voltage source is a capacitor, wherein a voltage at the capacitor is monitored, and wherein energy stored by the capacitor is provided as an input to the handpiece; and
a controller,
wherein data from monitoring the voltage source is provided to the controller,
wherein the controller is configured to generate an output that is provided to the charging element to dynamically adjust the charging element output, and
wherein the amount of energy provided by the voltage source as the input to the handpiece is dynamically adjusted based on the adjusted charging element output;
wherein the output of the controller compensates for undershoot, wherein undershoot occurs when the capacitor is charged to a level that is less than a predetermined level after a predetermined time.

42. A system for controlling an amount of energy delivered to a handpiece of a surgical system, comprising:
a power supply;
a charging element, wherein the power supply is configured to drive the charging element;
a voltage source at an output of the charging element, wherein the voltage source is a capacitor, wherein a voltage at the capacitor is monitored, and wherein energy stored by the capacitor is provided as an input to the handpiece; and
a controller,
wherein data from monitoring the voltage source is provided to the controller,
wherein the controller is configured to generate an output that is provided to the charging element to dynamically adjust the charging element output, and
wherein the amount of energy provided by the voltage source as the input to the handpiece is dynamically adjusted based on the adjusted charging element output;
wherein the output of the controller compensates for overshoot, wherein overshoot occurs when the capacitor is charged to a level that is greater than a predetermined level after a predetermined time.

* * * * *

UNITED STATES PATENT AND TRADEMARK OFFICE
CERTIFICATE OF CORRECTION

| | |
|---|---|
| PATENT NO. | : 7,640,119 B2 |
| APPLICATION NO. | : 11/479224 |
| DATED | : December 29, 2009 |
| INVENTOR(S) | : Amir H. Khashayar |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this

Ninth Day of November, 2010

David J. Kappos
*Director of the United States Patent and Trademark Office*